(12) United States Patent
Ferree

(10) Patent No.: US 9,801,668 B1
(45) Date of Patent: Oct. 31, 2017

(54) NEUROPHYSIOLOGICAL APPARATUS AND PROCEDURES

(71) Applicant: NuVasive, Inc., San Diego, CA (US)

(72) Inventor: Bret A. Ferree, Cincinnati, OH (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 14/855,156

(22) Filed: Sep. 15, 2015

Related U.S. Application Data

(63) Continuation of application No. 12/359,269, filed on Jan. 23, 2009, now Pat. No. 9,131,947, which is a continuation of application No. 10/842,192, filed on May 10, 2004, now abandoned.

(60) Provisional application No. 60/530,427, filed on Dec. 17, 2003, provisional application No. 60/468,981, filed on May 8, 2003.

(51) Int. Cl.
| | |
|---|---|
| *A61B 17/70* | (2006.01) |
| *A61B 17/16* | (2006.01) |
| *A61B 5/00* | (2006.01) |
| *A61B 5/0488* | (2006.01) |
| *A61B 5/04* | (2006.01) |
| *A61B 17/00* | (2006.01) |

(52) U.S. Cl.
CPC ...... *A61B 17/7092* (2013.01); *A61B 5/04001* (2013.01); *A61B 5/0488* (2013.01); *A61B 5/4566* (2013.01); *A61B 5/4893* (2013.01); *A61B 17/1626* (2013.01); *A61B 2017/00039* (2013.01)

(58) Field of Classification Search
CPC ............ A61B 17/7092; A61B 5/04001; A61B 5/4893; A61B 17/1626
See application file for complete search history.

(56) References Cited

U.S. PATENT DOCUMENTS

| | | | | |
|---|---|---|---|---|
| 4,224,949 A | * | 9/1980 | Scott ................. | A61B 10/0012 600/373 |
| 4,823,791 A | * | 4/1989 | D'Amelio .............. | A61B 18/14 219/234 |
| 5,480,440 A | * | 1/1996 | Kambin ............. | A61B 17/7007 128/898 |
| 5,607,422 A | * | 3/1997 | Smeets ............. | A61B 18/1492 606/41 |
| 5,928,158 A | * | 7/1999 | Aristides ................ | A61B 17/32 600/547 |
| 5,944,715 A | * | 8/1999 | Goble .................. | A61B 18/148 604/21 |

(Continued)

*Primary Examiner* — Ellen C Hammond
(74) *Attorney, Agent, or Firm* — Stephen H. Hall; Timothy L. Capria; Bradley Arant Boult Cummings LLP

(57) ABSTRACT

Neurophysiological instruments and techniques are improved through various enhancements. Stimulation of an instrument is possible while it is advancing into the spine or elsewhere, alerting the surgeon to the first sign the instrument or device (screw) may be too near a nerve. A directional probe helps surgeons determine the location of the hole in the pedicle. Electrically insulating sleeves prevent shunting into the soft tissues. According to a different improvement, the same probe to be used to stimulate different devices, such as screws and wires. Electrical impulses may be recorded from non-muscle regions of the body, including the spine and other portions of the central nervous system as opposed to just the extremities.

12 Claims, 33 Drawing Sheets

(56) References Cited

U.S. PATENT DOCUMENTS

| | | | | |
|---|---|---|---|---|
| 6,015,406 A * | 1/2000 | Goble | ............ | A61B 18/1485 |
| | | | | 606/41 |
| 6,090,106 A * | 7/2000 | Goble | ............ | A61B 18/1206 |
| | | | | 606/41 |
| 6,564,078 B1 * | 5/2003 | Marino | ............ | A61B 5/04012 |
| | | | | 600/373 |
| 6,719,692 B2 * | 4/2004 | Kleffner | ............ | A61B 17/16 |
| | | | | 600/437 |
| 7,172,594 B2 * | 2/2007 | Biscup | ............ | A61N 1/205 |
| | | | | 606/86 A |
| 7,942,826 B1 * | 5/2011 | Scholl | ............ | A61B 5/0492 |
| | | | | 600/554 |
| 8,291,915 B2 * | 10/2012 | Farley | ............ | A61B 18/1492 |
| | | | | 128/898 |
| 2002/0072686 A1 * | 6/2002 | Hoey | ............ | A61B 5/0537 |
| | | | | 600/547 |
| 2003/0083724 A1 * | 5/2003 | Jog | ............ | A61N 1/0536 |
| | | | | 607/122 |
| 2004/0049121 A1 * | 3/2004 | Yaron | ............ | A61B 5/04001 |
| | | | | 600/544 |
| 2004/0122482 A1 * | 6/2004 | Tung | ............ | A61B 5/0488 |
| | | | | 607/48 |
| 2004/0225228 A1 * | 11/2004 | Ferree | ............ | A61B 17/1626 |
| | | | | 600/554 |
| 2005/0075578 A1 * | 4/2005 | Gharib | ............ | A61B 5/0492 |
| | | | | 600/546 |
| 2006/0178594 A1 * | 8/2006 | Neubardt | ............ | A61B 5/05 |
| | | | | 600/547 |
| 2008/0125637 A1 * | 5/2008 | Geist | ............ | A61B 5/0492 |
| | | | | 600/372 |

* cited by examiner

NEUROPHYSIOLOGICAL APPARATUS AND PROCEDURES

CROSS-REFERENCE TO RELATED APPLICATIONS

This application is a continuation of U.S. patent application Ser. No. 12/359,269 filed Jan. 23, 2009, now U.S. Pat. No. 9,131,947, which is a continuation of U.S. patent application Ser. No. 10/842,192 filed May 10, 2004, abandoned, which claims the benefit under 35 U.S.C. §119(e) to U.S. Provisional Patent Application No. 60/468,981, filed May 8, 2003, and to U.S. Provisional Patent Application No. 60/530,427, filed Dec. 17, 2003, the entire contents of which are each hereby expressly incorporated by reference into this disclosure as if set forth fully herein.

FIELD OF THE INVENTION

This invention relates to neurophysiological techniques and, in particular, to improved instruments and procedures to ensure accurate, real-time, temporary or permanent placement of surgically implanted devices.

BACKGROUND OF THE INVENTION

Pedicle instrumentation is often used to facilitate spinal fusion. Pedicle screws extend through the pedicles of vertebrae and into the body of the vertebrae. The screws are connected by rods or plates to eliminate motion between the vertebrae that are fused together.

Misplaced pedicle screws can injury the nerves and blood vessels that surround the vertebrae. Numerous techniques are used to help surgeons guide screws into the pedicles of the vertebrae. For example, surgeons often use x-rays including fluoroscopy to confirm the position of pedicle screws.

Nerve compression by pedicle screws can also be determined through electrical stimulation of the pedicle screws. Prior-art techniques involve recording electrical impulses in the legs or arms after electrical stimulation of the pedicles. High conductivity of the electrical impulses suggests the pedicle screws are too close to spinal nerves. High conductivity is determined by recording electrical impulses in the legs or arms of a patient after applying electrical impulses of relatively low amplitude to the pedicle screws.

Prior art "neurophysiology" techniques have several deficiencies. First, existing systems rely on the conductivity through a patient's body from the pedicle screw to electrodes in extremities or electrodes on the skin of the extremities. False negative values, low conductivity, can occur if the nerves or the skin do not conduct electricity well. Damaged nerves can be relatively poor conductors of electricity. Second, electrical impulses of relatively high magnitudes must be used to overcome the resistance of the skin, muscles, and nerves. Stimulation by electrical impulses of large amplitude can damage nerves. Third, the variable resistance of patient's bodies leads to a relatively wide range of "normal" values recorded from the extremities. The wide range of normal values decreases the sensitivity and the specificity of the prior art technologies.

NuVasive, Inc. of San Diego, Calif. offers a product that uses "screw test" technology to determine if a screw or similar device is being positioned close to a nerve during a surgical procedure. Surgeons typically use NuVasive's system to stimulate screws, guidewires, and taps placed into the pedicles of vertebrae. Recording surface electrodes are placed over the legs of the patient. Nerves conduct electricity very efficiently, such that electrical stimulation of the metal objects placed into the vertebrae can be recorded in the legs.

Using the NuVasive system, an electrical charge is sent through the screw, and a circle lights up on a computer screen giving a simple number to indicate the amount of charge reaching sensors placed on the patient's leg muscles. A high number, such as a 20, suggests the screw is clear of the nerve. A lower reading, like a 3, indicates the nerve is being stimulated and the surgeon needs to consider moving the screw. Thus, the lower the amplitude needed to record activity in the legs, the closer the metal objects are to the spinal nerves.

Research has shown that if the surface electrodes record electrical activity with stimulation of less than 8 milliamps, the metal objects are too close to the spinal nerves. The system can also be used in the cervical spine. The surface electrodes are placed on the arms for recording stimulation of devices placed into the cervical spine.

The NuVasive system has a several shortcomings. For one, the system does not yield real-time data. Nor does the system allow for efficient, repeated stimulation of instruments that are turned. This is due to the fact that the NuVasive system uses a ball-tipped stimulating probe, and the ball of the probe slips off the circular shaft of the instruments. In addition, while the system helps surgeons identify holes in the pedicle, it does not identify the location of the hole in the pedicle. Also, the instruments and screws that are placed into the spine cannot touch the skin, muscles, and subcutaneous tissues surrounding the spine during electrical stimulation. If the metal instruments touch the surrounding tissues during stimulation, the electricity can be shunted from the vertebrae. Shunting of electricity can lead to false recordings in the legs or arms (during stimulation in the cervical spine). Furthermore, the existing NuVasive system requires two different probes; one to stimulate screws and a second probe to stimulate wires.

SUMMARY OF THE INVENTION

This invention improves upon neurophysiological techniques through provision of several enhancement features. According to one aspect of this invention, stimulation of an instrument is possible while it is advancing into the spine or elsewhere, alerting the surgeon to the first sign the instrument or device (screw) may be too near a nerve. Early identification of misdirected instruments or screws may thus help prevent nerve damage.

A different aspect involves a directional probe that helps surgeons determine the location of the hole in the pedicle. Yet a further aspect provides an insulation sleeves to prevent shunting into the soft tissues. According to a different improvement, the same probe to be used to stimulate different devices, such as screws and wires.

One embodiment of the invention involves a clip that allows the use of continuous monitoring during curette, pedicle probe, tap, pedicle screw, and/or lateral mass screw insertion. The clip fits around the cylindrical shafts of these and instruments used to insert devices, including screws. The clip allows the shafts of the instruments to rotate without rotating the probe that sends electrical impulses for the testing. The surgeon may rotate an instrument to insert a tap, for instance, while an assistant repeatedly fires the probe. Thus, the surgeon can detect a breach of the pedicle wall as soon as it occurs rather than after the tap, etc. is fully inserted. Theoretically, early detection of a breach in the pedicle may prevent nerve injury and prevent enlarging a mal-aligned hole.

Other apparatus and methods of this invention improve upon existing neurophysiology technology in that electrical impulses are recorded from the spine rather than the extremities. Recording the impulses closer to the stimulated pedicle screws overcomes the deficiencies of prior-art techniques as outlined above.

DETAILED DESCRIPTION OF THE INVENTION

Figure 1:
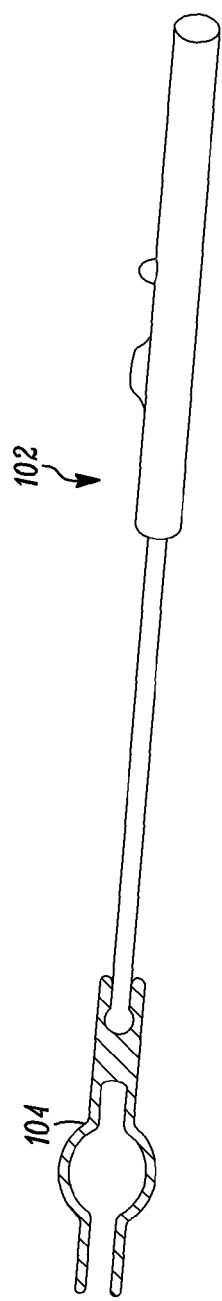
FIG. 1 is a lateral view of the side of the current probe and a novel clip of the present invention.
Figure 2:
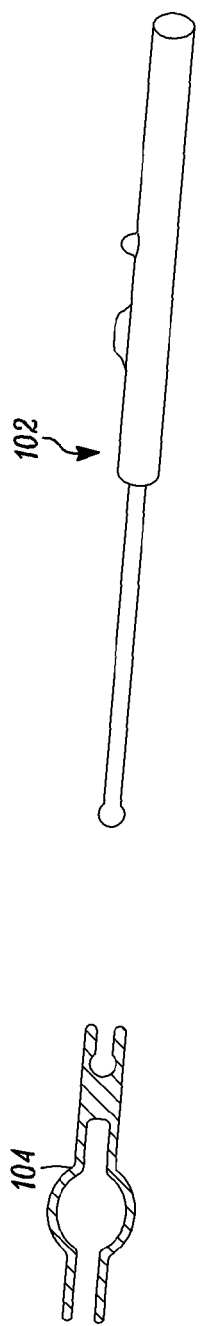
FIG. 2 is an exploded view of the invention of FIG. 1.

FIG. 1 is a lateral view of the side of the current probe 102 and a novel clip 104 according to this invention. One end of the clip snaps around instruments. The second end of the clip snaps over the tip of the probe. Alternatively, a second probe tip could be manufactured that incorporates the novel tip end. FIG. 2 is a detached view of the probe and tip of FIG. 1.

Figure 3A:
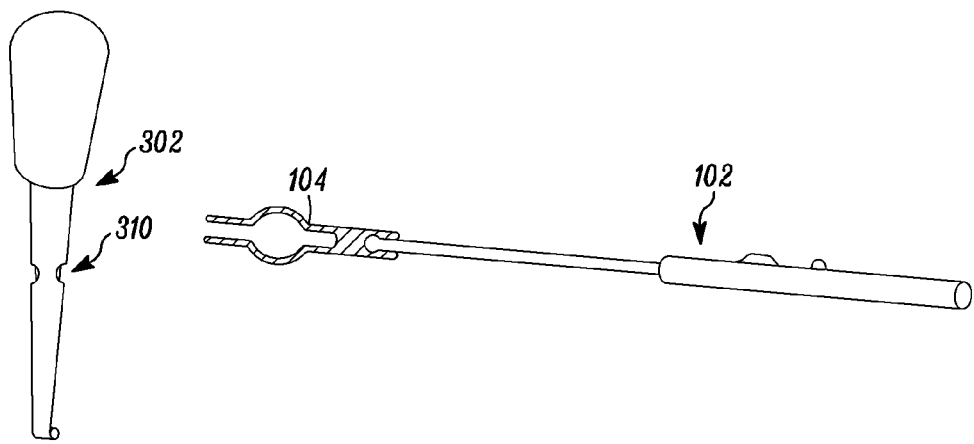
FIG. 3A is a lateral view of a curette to "sound" the pedicle and the probe with a clip attachment.
Figure 3B:
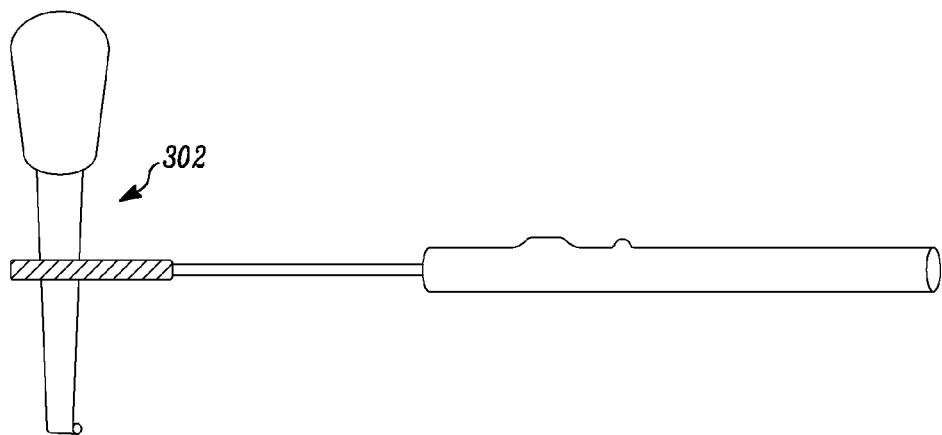
FIG. 3B is a lateral view of the probe of FIG. 1 attached to the curette of FIG. 3A.
Figure 3C:
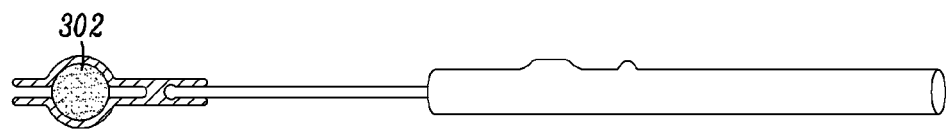
FIG. 3C is a cross section of the shaft of an instrument surrounded by the novel clip of the present invention.

FIG. 3A is a lateral view of a curette 302 used to "sound" the pedicle and the probe 102 with a clip attachment 104. The shaft of the instrument 302 may be machined with a groove 310 to cooperate with the clip. FIG. 3B is a lateral view of the probe of FIG. 1 attached to the curette of FIG. 3A. FIG. 3C is a cross section.

Figure 4:
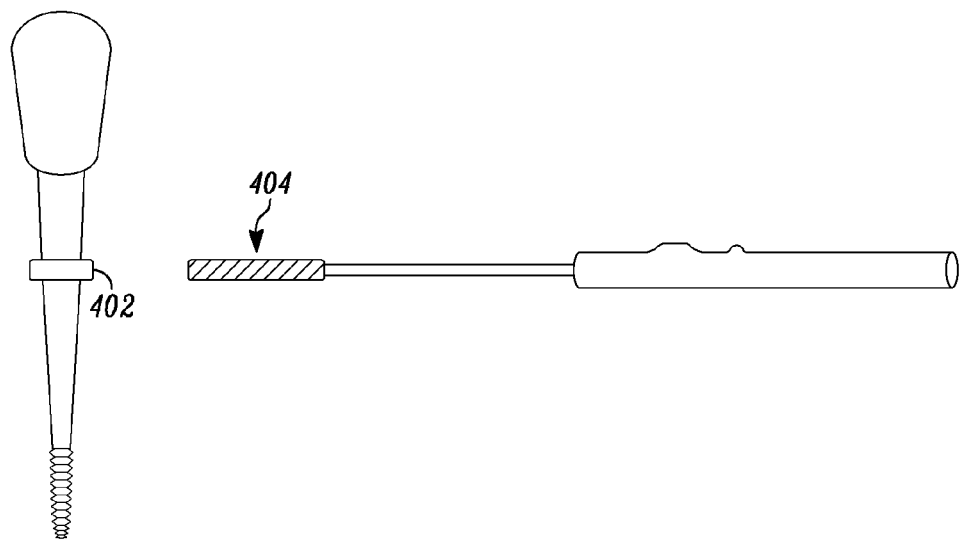
FIG. 4 is a lateral view of an alternative embodiment instrument shaft.
Figure 5:
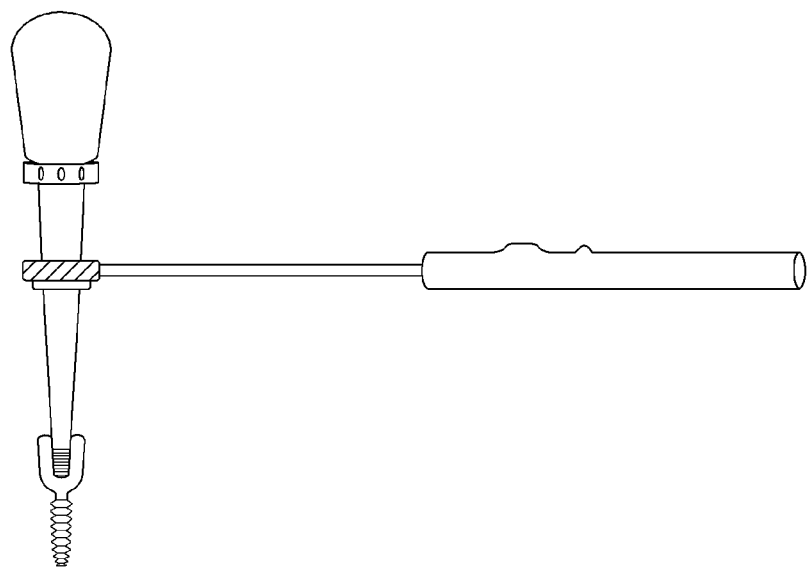
FIG. 5 is a lateral view of the embodiment of the instrument drawn in FIG. 4.

FIG. 4 is a lateral view of an alternative embodiment, wherein the shaft of the 20 tap has a raised portion 402 to cooperate with a clip 404. The raised portion 402 avoids the stress riser created by a groove in the shaft. FIG. 5 is a lateral view of the embodiment of the instrument drawn in FIG. 4. The clip of the probe surrounds the shaft of the pedicle screw insertion tool. The clip rides on the enlargement of the shaft.

Figure 6:
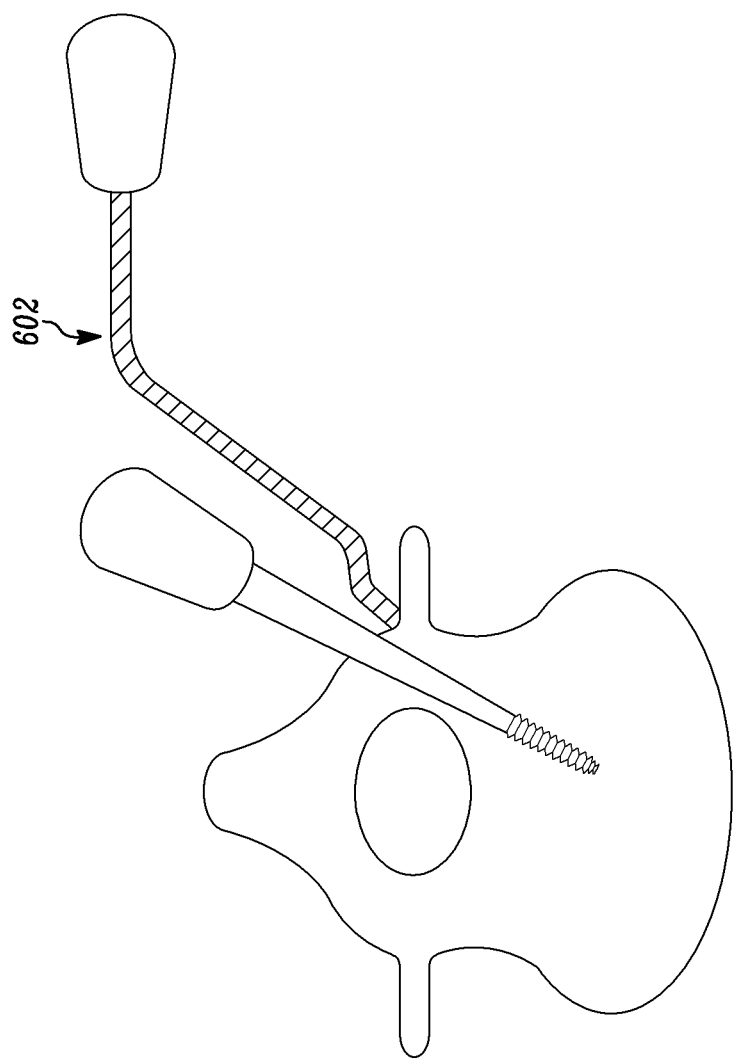
FIG. 6 is the lateral view of an instrument to retract the soft tissues during pedicle screw or instrument stimulation.

FIG. 6 is the lateral view of an instrument 602 used to retract the soft tissues during pedicle screw or instrument stimulation. The retraction instrument is made of plastic or other material that does not conduct electricity in the preferred embodiment.

Figure 7:
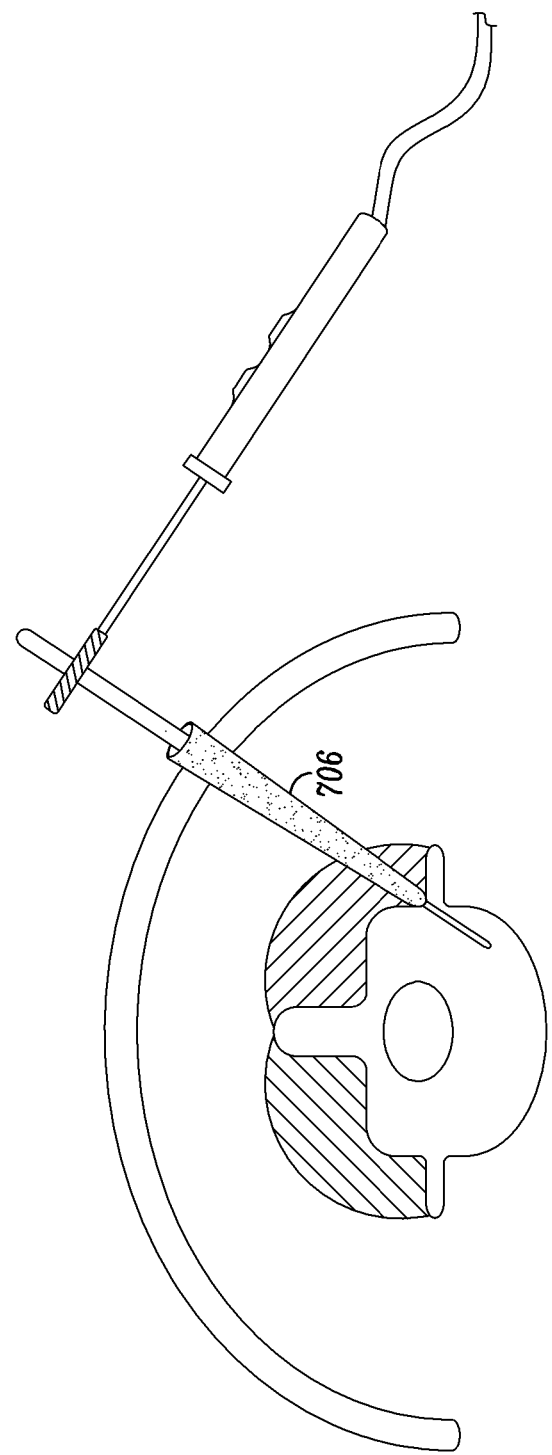
FIG. 7 shows the insulated soft tissue retractor drawn in FIG. 6.

As an alternative to the insulated soft tissue retractor of FIG. 6, an insulated sleeve drawn in FIG. 7 may be used. FIG. 7 is an axial cross section through a vertebra and the surrounding muscles, skin, and subcutaneous tissues. A plastic sleeve would be particularly useful when stimulating percutaneous guide pins inserted into the pedicles. The insulating sleeve 706 prevents the transmission of electricity from the guide pin to the muscles or surrounding soft tissue. A similar apparatus could be used for testing modular taps. For example, the handle of a tap could be removed, thus allowing the insulating sheath to be placed over the tap.

Although the NuVasive monitoring system helps surgeons identify breaches of the walls of the pedicles, the system does not suggest where the pedicle wall has been breached. According to this invention, however, since the probe tip may be insulated circumferentially around the majority of the tip of the probe, the non-insulated portion of the tip can be rotated within the pedicle to determine the direction that requires the least amount of stimulation to record activity in the lower extremity.

Figure 8A:
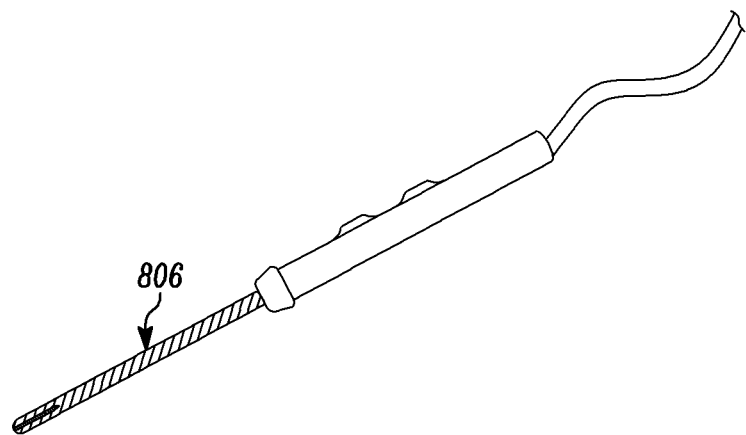
FIG. 8A is a lateral view of the probe and the novel tip.

FIG. 8A is a lateral view of the probe and a tip according to the invention. The dark area of the tip conducts electricity. The remainder of the tip 806 is insulated to prevent the conduction of electricity.

Figure 8B:
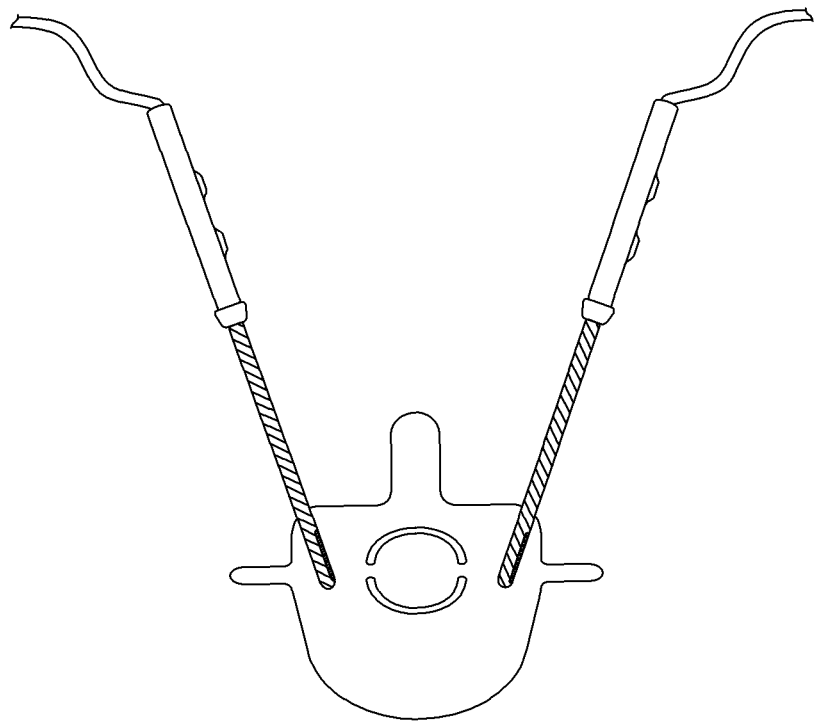
FIG. 8B is an axial cross section of a vertebra and probes with the novel tips.

FIG. 8B is an axial cross section of a vertebra and probes using these tips. The medial walls of the pedicles have been breached. The probe on the left side of the drawing has the non-insulted portion of the tip directed toward the hole in the pedicle. The probe on the right side of the drawing has the insulated portion of the tip facing the hole in the pedicle. Less current will be required to stimulate the nerves on the left side of the drawing. For example, the surface electrodes could record activity in the lower extremity with stimulation of the probe at 4 milliamps with the exposed (conducting) area of the probe directed toward the medial wall of the pedicle (probe on the left side of the drawing) and the surface electrodes could record electrical activity in the lower extremities with stimulation of the probe at 10 milliamps with the exposed (conducting) area of the probe directed toward the lateral wall of the pedicle (probe on the right side of the drawing). Thus, the surgeon knows the medial wall of the pedicle has been breached. Consequently, the surgeon knows to redirect the pedicle screw more laterally, away from the holes in the pedicle.

Figure 9A:
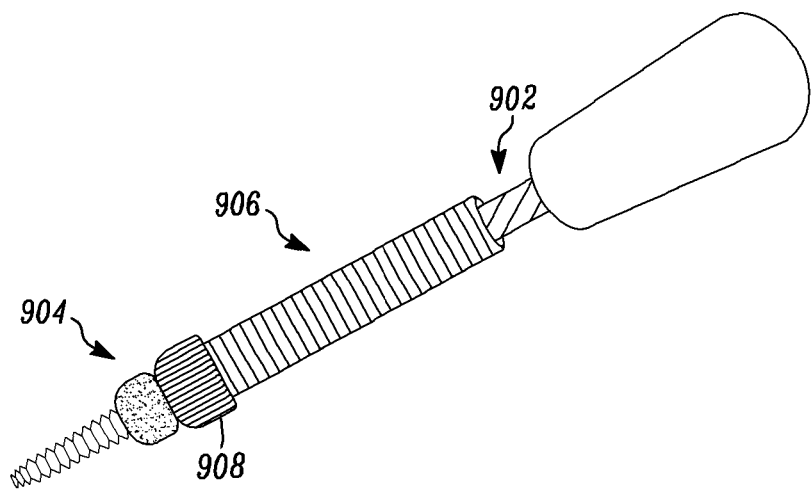
FIG. 9A is a lateral view of a screw driver, pedicle screw, and a novel insulating sleeve.

FIG. 9A is a lateral view of a screwdriver 902, pedicle screw 904, and an insulating sleeve 906. The insulating sleeve is preferably constructed of a flexible material that does not conduct electricity. For example, the sleeve could be made of plastic or natural or synthetic rubber. The sleeve can be seen folded back over itself at 908 just above the pedicle screw.

Figure 9B:
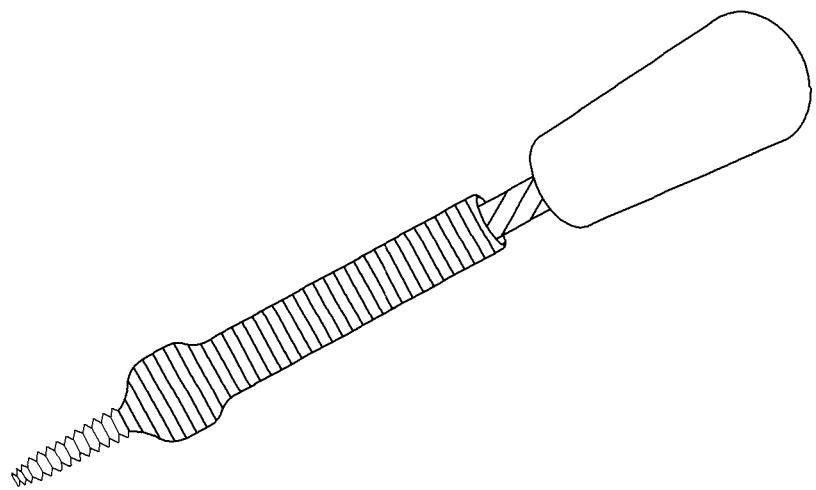
FIG. 9B is a lateral view of apparatus drawn in FIG. 9A.

FIG. 9B is a lateral view of apparatus drawn in FIG. 9A. The insulating sleeve 906 has been unfolded and placed over the head of the pedicle screw. The insulating sleeve prevents the transmission of electricity into the tissues that surround the spine. Electricity from stimulating the shaft of the screwdriver exits through the threads of the screw. The sleeve enables the screwdriver to lie against the muscles of the spine without stimulating the muscles of the spine.

Figure 9C:
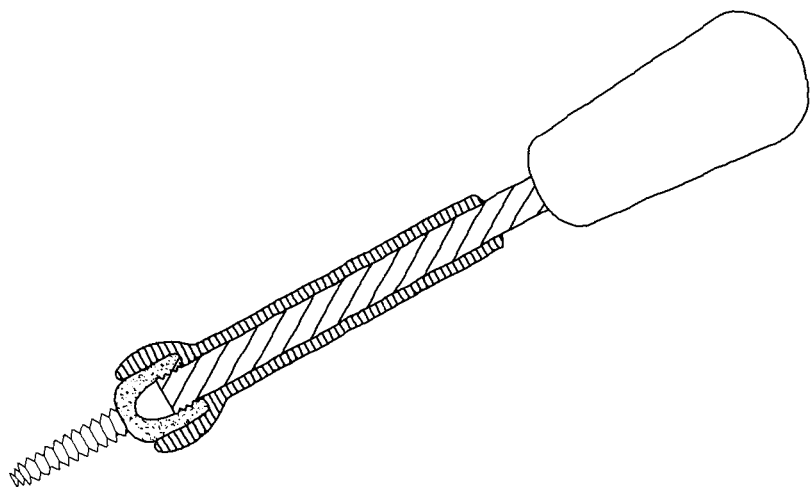
FIG. 9C is a cross section of the apparatus drawn in FIG. 9B.

FIG. 9C is a cross section of the apparatus drawn in FIG. 9B. The flexible insulation sleeve can be stretched to fit tightly against the shaft of the screwdriver and the pedicle screw.

Figure 9D:
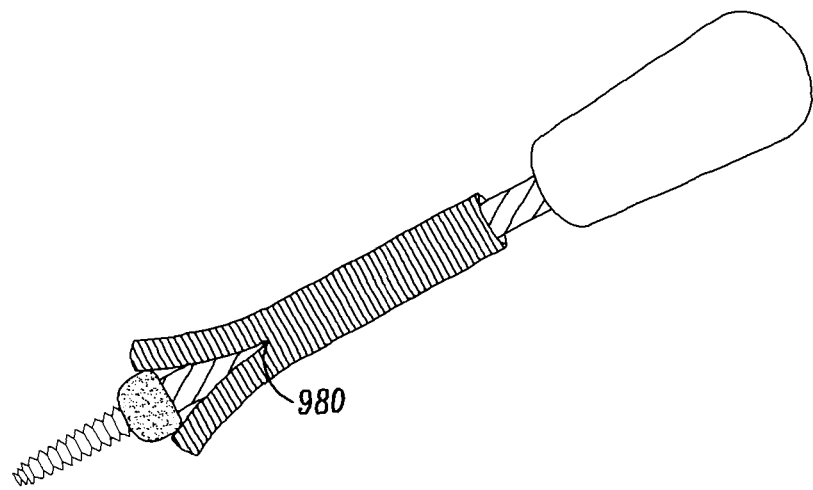
FIG. 9D is a lateral view of the apparatus drawn in FIG. 9B.

FIG. 9D is a lateral view of the apparatus drawn in FIG. 9B. The insulation sleeve may be removed by pulling on a cord 980 which tears the sleeve. Alternative mechanisms can be used to remove the sleeve from the screw. For example, the sleeve could be pulled from the screw while exerting counter pressure on the screw by the screwdriver. The sleeve could also be folded on itself as the sleeve is removed from the screw.

Figure 10A:
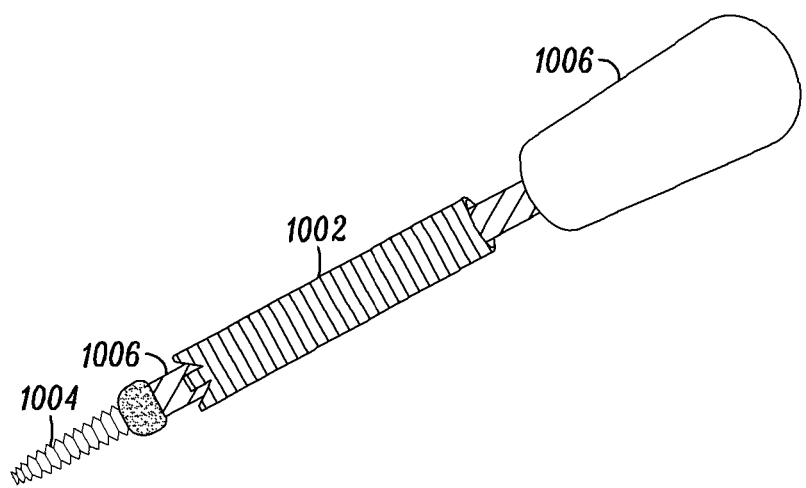
FIG. 10A is a lateral view of an alternative embodiment of the insulation sleeve, pedicle screw, and sleeve expander.

FIG. 10A is a lateral view of an alternative embodiment of an insulating sleeve 1002, pedicle screw 1004, and screwdriver with a sleeve expander 1006. The sleeve is drawn in its expanded shape. The tip of the sleeve expander fits into the pedicle screw. In the preferred embodiment, the sleeve expander is flush with the top of the pedicle screw. The sleeve in this embodiment of the device is made of material that plastically deforms at its tip. The sleeve does not transmit electricity.

Figure 10B:
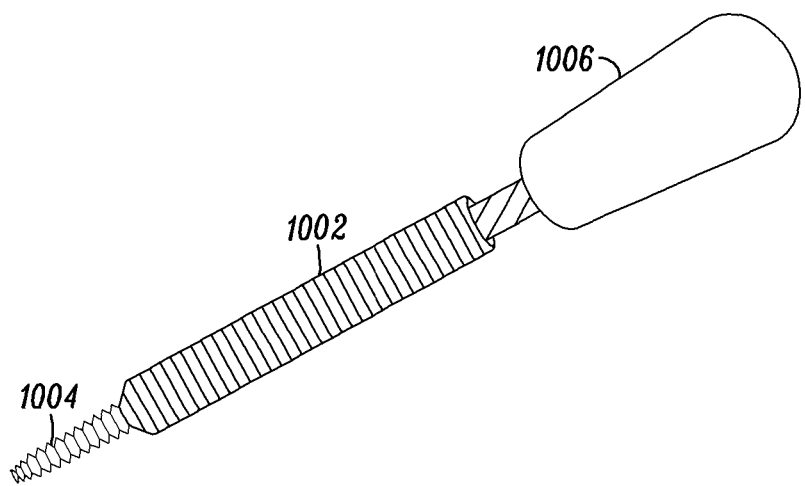
FIG. 10B is a lateral view of the apparatus drawn in FIG. 10A.

FIG. 10B is a lateral view of the apparatus drawn in FIG. 10A with the sleeve in its contracted shape. The tip of the sleeve contracts to surround the head of the pedicle screw. Ideally the sleeve is more rigid than sleeve drawn in FIG. 9A. The rigidity of the sleeve enables it to be forced over the screw by pushing on the top of the sleeve. This embodiment of the device would be easier to use after the screw has been placed into the spine.

Figure 10C:
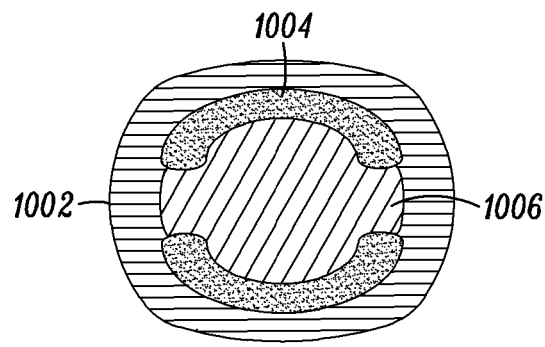
FIG. 10C is an axial cross section of the sleeve, screw, and sleeve expander drawn in FIG. 10A.
Figure 10D:
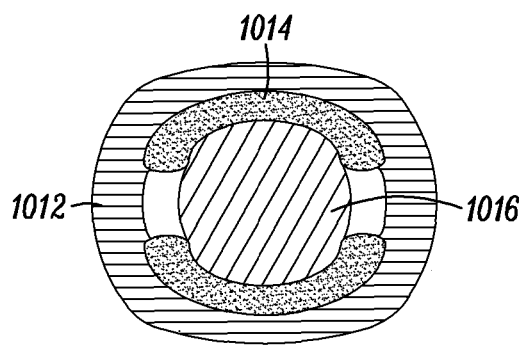
FIG. 10D is an axial cross section of an alternative embodiment of the sleeve expander drawn in FIG. 10C.

FIG. 10C is an axial cross section of the sleeve 1002, screw 1004, and sleeve expander 1006 in FIG. 10A. The sleeve expander 1006 fits into the opening in the pedicle screw. FIG. 10D is an axial cross section of an alternative embodiment of the sleeve expander 1016, a screw 1014, and the sleeve 1012. The tip of the sleeve expander in this case is round to fit in the circular opening in the pedicle screw.

Figure 11A:
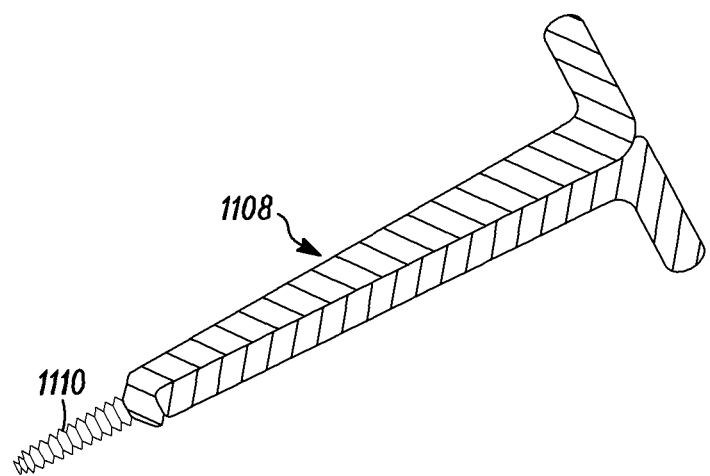
FIG. 11A is a lateral view of an alternative embodiment of the insulating sleeve.
Figure 11B:
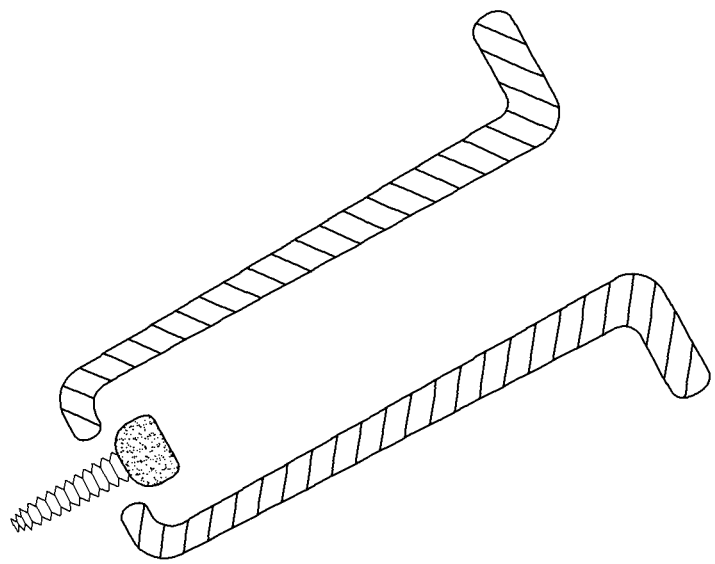
FIG. 11B is an exploded view of the embodiment of the invention drawn in FIG. 11A.
Figure 11C:
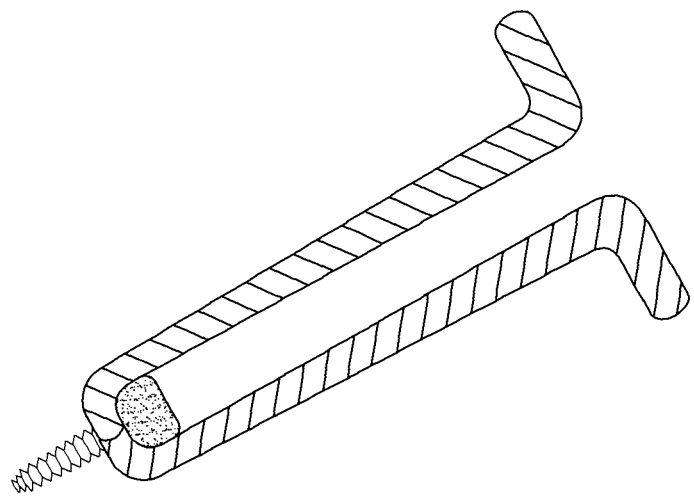
FIG. 11C is a cross section of the apparatus drawn in FIG. 11A.
Figure 12A:
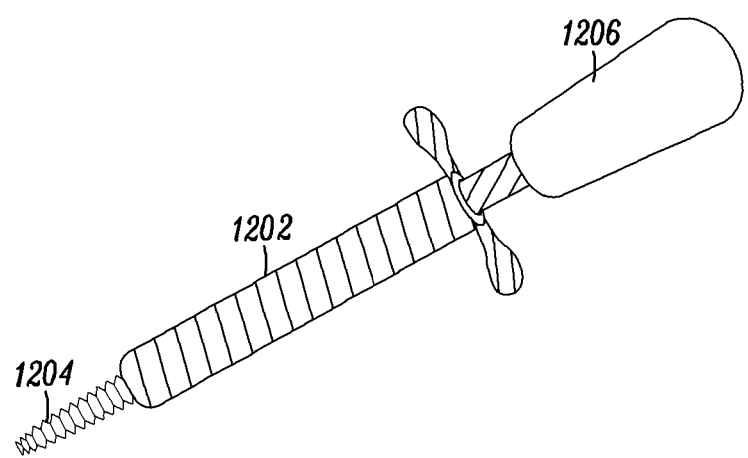
FIG. 12A is a lateral view of an alternative embodiment of the novel sleeve, a screw, and a screwdriver.

FIG. 11A is a lateral view of an alternative embodiment of the insulating sleeve 1108 assembled over a pedicle screw 1110. FIG. 11B is an exploded cross-sectional view of the embodiment of the invention drawn in FIG. 11A. FIG. 11C is a cross section of the apparatus drawn in FIG. 11A. FIG. 12A is a lateral view of an alternative embodiment of the novel sleeve 1202, a screw 1204, and a screwdriver 1206. The insulating sleeve is placed over the pedicle screw and screwdriver prior to insertion of the pedicle screw into the spine.

Figure 12B:
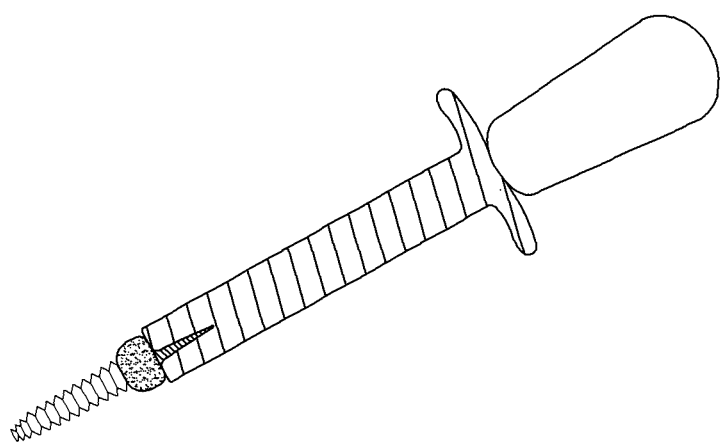
FIG. 12B is a lateral view of the apparatus drawn in FIG. 12A.

FIG. 12B is a lateral view of the apparatus drawn in FIG. 12A. The sleeve has been pulled off of the pedicle screw. Longitudinal force on the sleeve may be used to split the sleeve along a pre-stressed area in the sleeve.

Figure 13A:
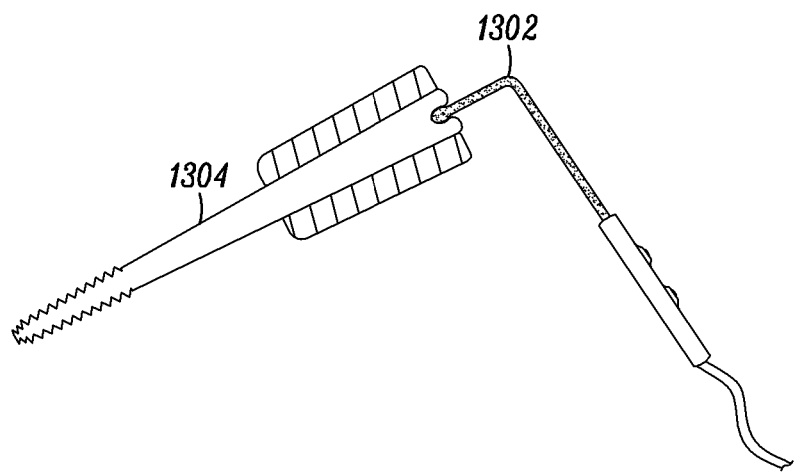
FIG. 13A is a sagittal cross section through an alternative embodiment of that drawn in FIG. 3.

FIG. 13A is a sagittal cross section through an alternative embodiment of the invention, wherein a probe 1302 is placed into the center of an instrument 1304. The illustration shows application of the probe to a tap. Placing the instrument onto or into the center of the instrument allows rotation of the instrument during repeated stimulation of the instrument.

Figure 13B:
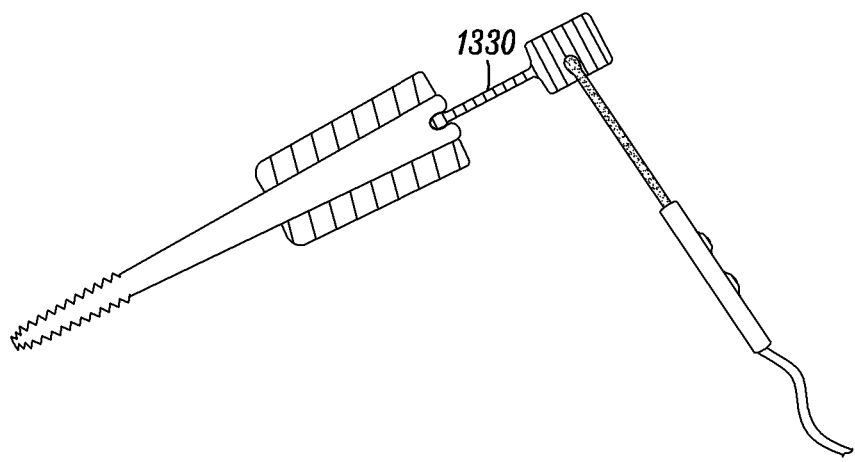
FIG. 13B is a sagittal cross section through an alternative embodiment of that drawn in FIG. 13A.

FIG. 13B is a sagittal cross section through an alternative embodiment of that drawn in FIG. 13A. The probe connects to an intermediate piece 1330 that connects to the center of the instrument.

Figure 14B:
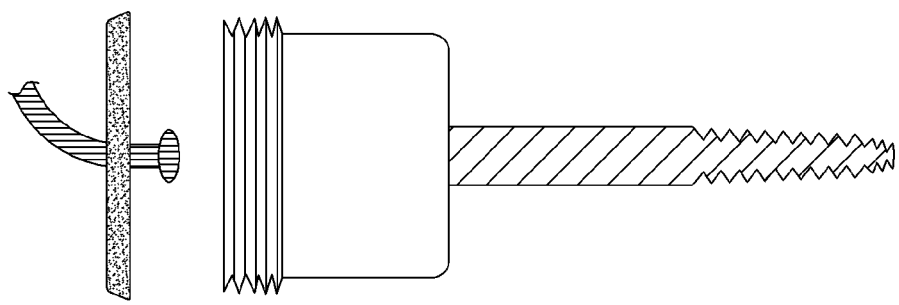
FIG. 14B is an exploded lateral view of the embodiment of the invention 25 drawn in FIG. 14A.
Figure 14A:
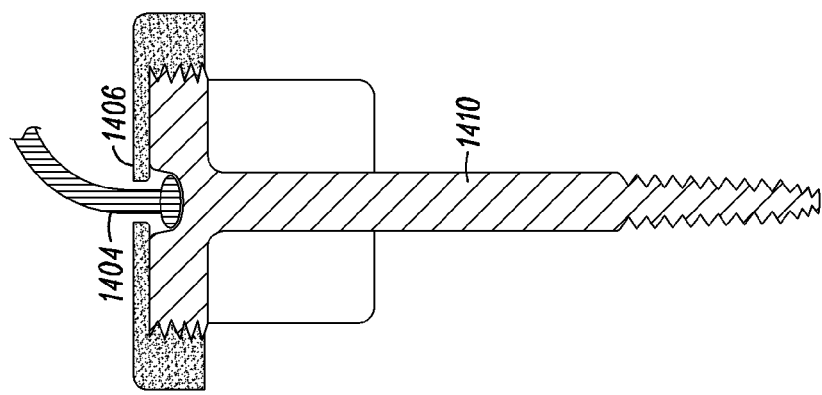
FIG. 14A is a sagittal cross section of an alternative embodiment of invention drawn in FIG. 13B.

FIG. 14A is a sagittal cross section of an alternative embodiment of invention drawn in FIG. 13B. The spherical end of an electrode 1404 is captured in the instrument by a cannulated, threaded cap 1406. The shaft of the instrument 1410 conducts electricity. The joint between the tip of the electrode allows movement between the electrode and the instrument, while maintaining continuous contact between the two components. FIG. 14B is an exploded lateral view of the embodiment of the invention drawn in FIG. 14A.

Figure 14D:
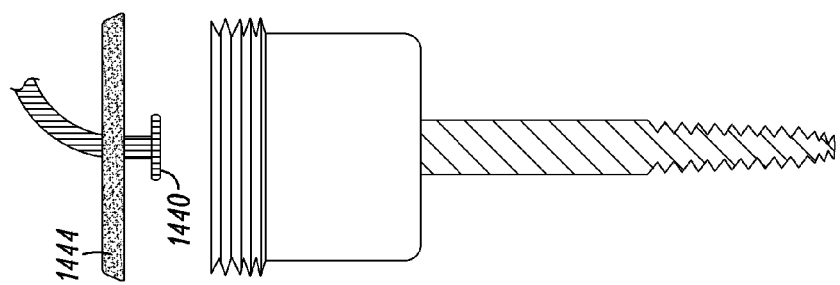
FIG. 14D is an exploded lateral view of the embodiment of the invention drawn in FIG. 14C.
Figure 14C:
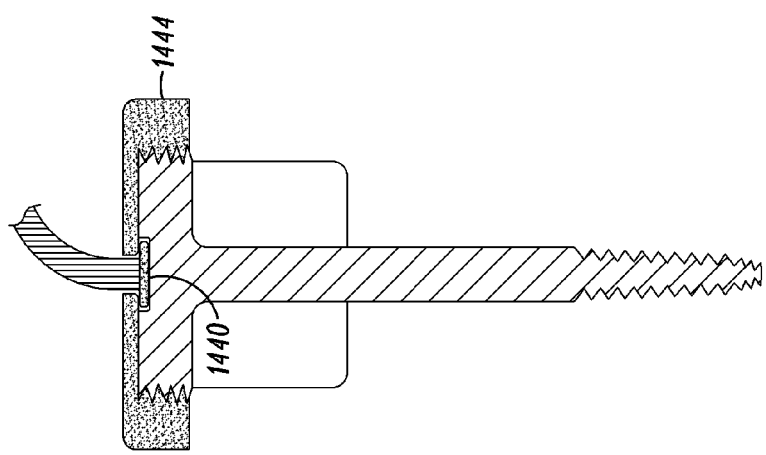
FIG. 14C is a sagittal cross section of an alternative embodiment of the invention drawn in FIG. 14A.

FIG. 14C is a sagittal cross section of an alternative embodiment of the invention utilizing a flat-tipped electrode 1440 captured by a threaded component 1444. The joint between the electrode and the instrument allows rotation. FIG. 14D is an exploded lateral view of the embodiment of the invention drawn in FIG. 14C. Connections between electrodes of alternative shaped tips and instruments of alternative shapes are contemplated so long as the joints between the components permit rotation and keep the two components in contact.

Figure 15B:
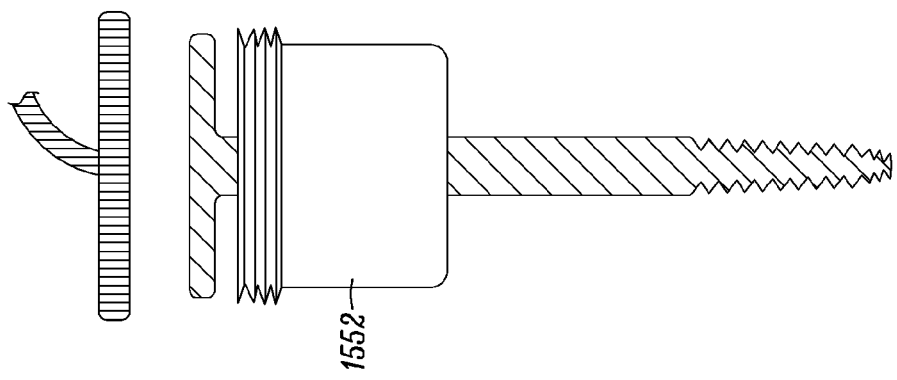
FIG. 15B is an exploded lateral view of the embodiment of the invention drawn in FIG. 15A.
Figure 15A:
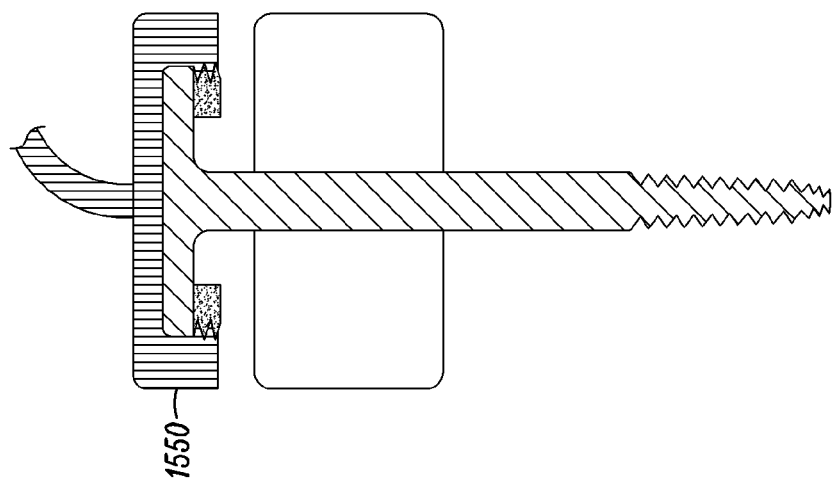
FIG. 15A is a sagittal cross section of an alternative embodiment of the invention drawn in FIG. 14C.

FIG. 15A is a sagittal cross section of an alternative embodiment of the invention, wherein an electrode 1550 is threaded over the shaft of the instrument 1552. The threaded connection between the electrode and the instrument holds the two components together. Rotation may occur across the flat surfaces of the two components. FIG. 15B is an exploded lateral view of the embodiment of the invention drawn in FIG. 15A.

Figure 16B:
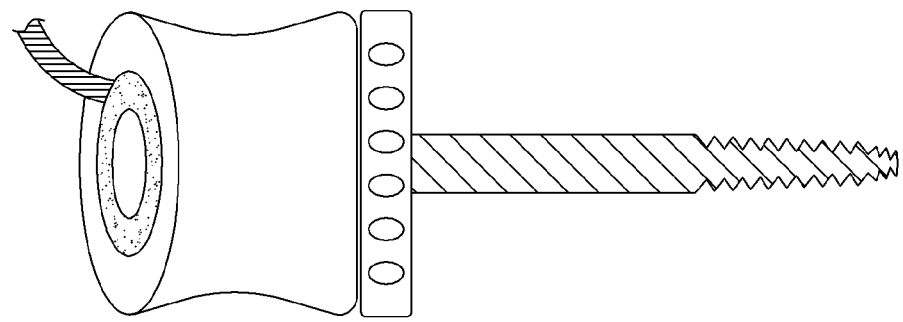
FIG. 16B is an oblique view of an alternative embodiment of the invention drawn in FIG. 16A.
Figure 16A:
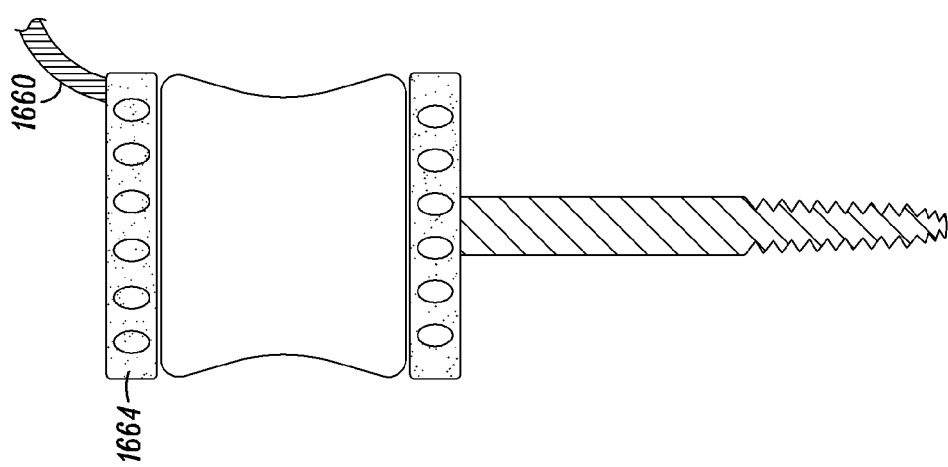
FIG. 16A is a lateral view of an alternative embodiment of the invention drawn in FIG. 14A.

FIG. 16A is a lateral view of an alternative embodiment of the invention drawn in FIG. 14A. A wire 1660 for the electrode is connected to a ratcheting component 1664 on the shaft of the instrument. The ratcheting component permits advancement of screws and taps with small rotations of the handle of the instrument forward and backward. The electrode does not wrap around the instrument because the handle of the instrument does not require rotation through 360 degrees.

FIG. 16B is an oblique view of an alternative embodiment of the invention drawn in FIG. 16A. The electrode is connected to a conducting component within the handle of the instrument. The conducting component transmits electrical impulses between the electrode and the shaft of the instrument. The ratcheting mechanism prevents wrapping the cord of the electrode around the instrument as the instrument is rotated.

Figure 17B:
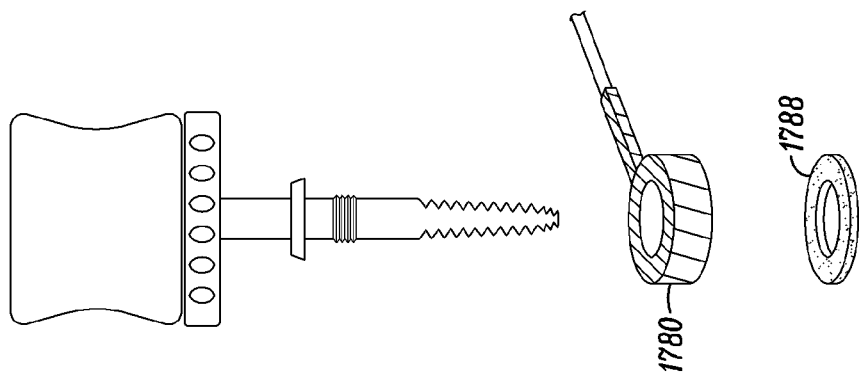
FIG. 17B is an exploded lateral view of the embodiment of the invention drawn in FIG. 17A.
Figure 17A:
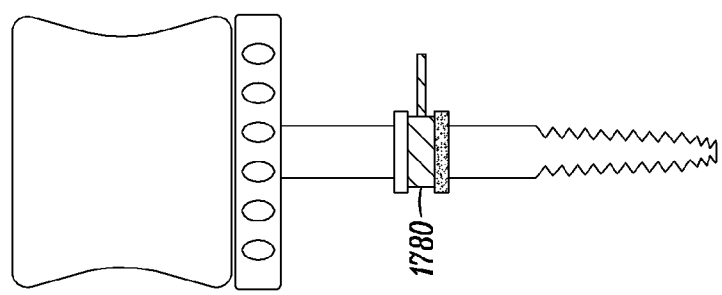
FIG. 17A is a lateral view of an alternative embodiment of the invention drawn in FIG. 14A.

FIG. 17A is a lateral view of an alternative embodiment of the invention including an electrode 1780 connected to a collar that rotates around the shaft of the instrument. The collar is held between projections from the shaft of the instrument. The collar remains in contact with the shaft of the instrument. Rotation between the shaft of the instrument and the collar prevents wrapping the cord of the electrode around the instrument as a screw or tap is advanced. FIG. 17B is an exploded lateral view of the embodiment of the invention drawn in FIG. 17A. The rotating collar is held on the shaft of the instrument by a removable threaded component 1788.

Figure 18:
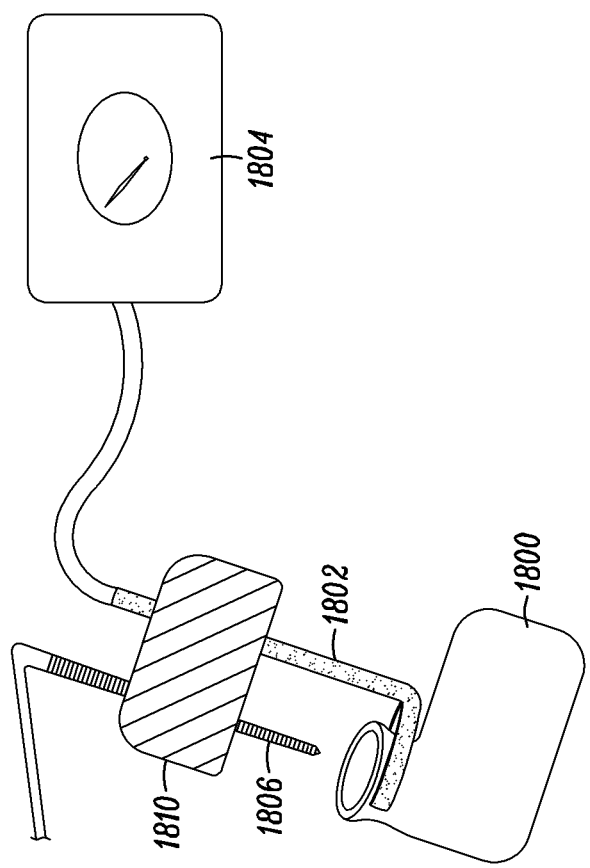
FIG. 18 is an oblique view of a portion of a vertebra and the preferred apparatus.

FIG. 18 is an oblique view of a portion of a vertebra and preferred apparatus including a recording electrode 1802 placed around a portion of the pedicle of a vertebra 1800. The recording electrode is connected to a monitor 1804. The area 1806 represents a pedicle probe, tap, screw, or other instrument that will be placed into the pedicle. The pedicle instrument or screw is connected to a stimulating electrode. The recording and stimulating electrodes can be connected by third component 1810. The connecting 15 component is represented by the area of the drawing with diagonal lines. In the preferred embodiment, the connecting component 1810 is radiolucent and made of a material that conducts electricity poorly.

Figure 19B:
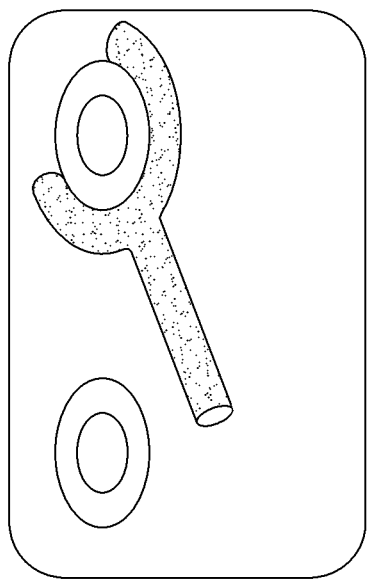
FIG. 19B is a view of the dorsal aspect of a portion of a vertebra and a recording electrode.
Figure 19A:
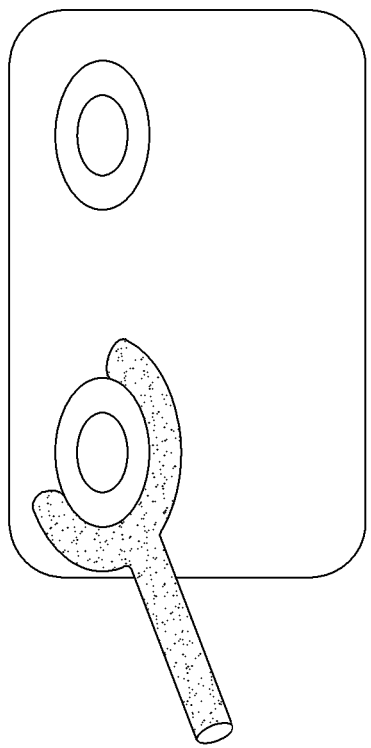
FIG. 19A is a view of the dorsal aspect of a portion of a vertebra and a recording electrode.

FIG. 19A is a view of the dorsal aspect of a portion of a vertebra and a recording electrode 1802. The lamina of the vertebra has been removed to better illustrate the pedicles of the vertebra. The arms of the recording electrode can be seen surrounding the inferior, medial, and lateral surfaces of the pedicle. The recording electrode was inserted from the inferior and/or lateral side of the vertebra.

FIG. 19B is a view of the dorsal aspect of a portion of a vertebra and a recording electrode 1802. The recording electrode can be seen over the medial, superior, and inferior surfaces of a pedicle. The recording electrode was inserted from the medial side of the pedicle. A laminectomy could be performed to aid placement of the electrode.

Figure 20A:
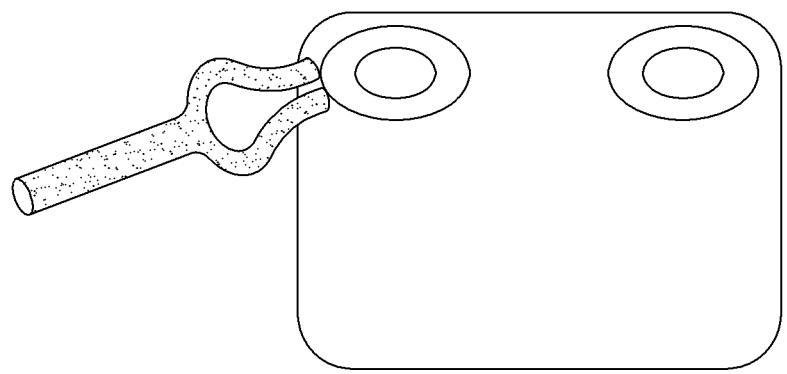
FIG. 20A is a view of the dorsal aspect of a portion of a vertebra and a 20 recording electrode on the inferior lateral surface of a pedicle.
Figure 20B:
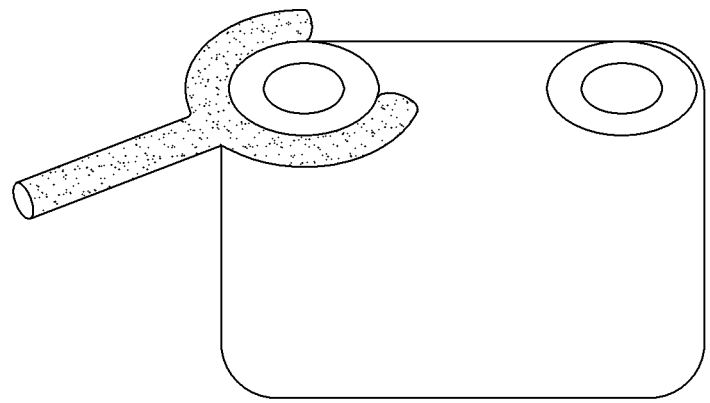
FIG. 20B is a view of the dorsal aspect of a portion of a vertebra and a recording electrode.

FIG. 20A is a view of the dorsal aspect of a portion of a vertebra and a recording electrode 1802 on the inferior lateral surface of a pedicle. FIG. 20B is a view of the dorsal aspect of a portion of a vertebra and a recording electrode. The recording electrode has been advanced over the pedicle. The arms of the recording electrode can be spring loaded to ease insertion of the electrode over the pedicle.

Figure 21A:
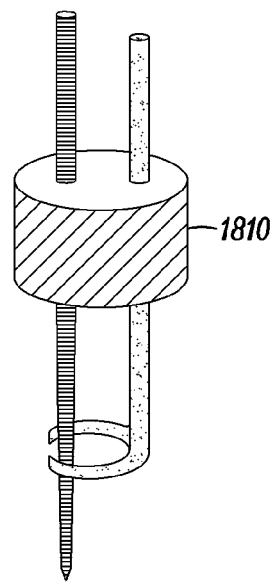
FIG. 21A is an oblique view of the apparatus drawn in FIG. 18.

FIG. 21A is an oblique view of the apparatus drawn in FIG. 18. The connector 1810 aligns the instrument or screw to be inserted into the pedicle with the arms of the recording electrode. For example, pedicle screws can be directed into the center of the arms of the recording electrode. Thus, if the arms of the recording electrode surround a portion of the pedicle, the pedicle screw or instrument can be directed into the center of the pedicle.

Figure 21B:
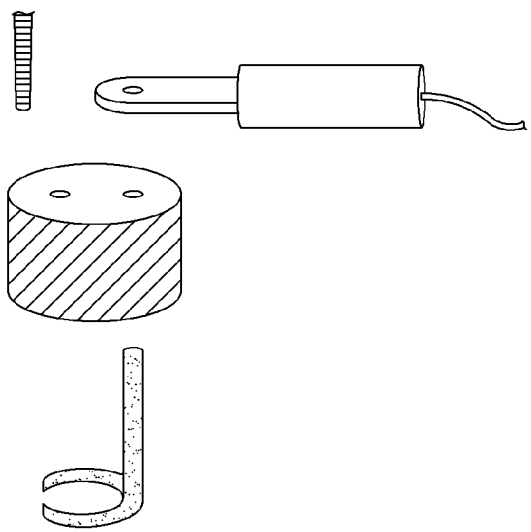
FIG. 21B is an exploded view of the apparatus drawn in FIG. 21A.

FIG. 21B is an exploded view of the apparatus drawn in FIG. 21A. A removable handle is also illustrated. The removable handle can be placed over the recording electrode after placement of the connecting component over the recording component.

Figure 21C:
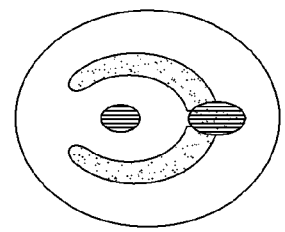
FIG. 21C is a view of the top of the connecting component, the recording and stimulating electrodes.

FIG. 21C is a view of the top of the connecting component, the recording and stimulating electrodes. The radiolucent connecting component allows surgeons to view insertion of the stimulating electrode between the arms of the recording electrodes with fluoroscopy. The arms of the recording electrode surround a portion of the pedicle.

Figure 22:
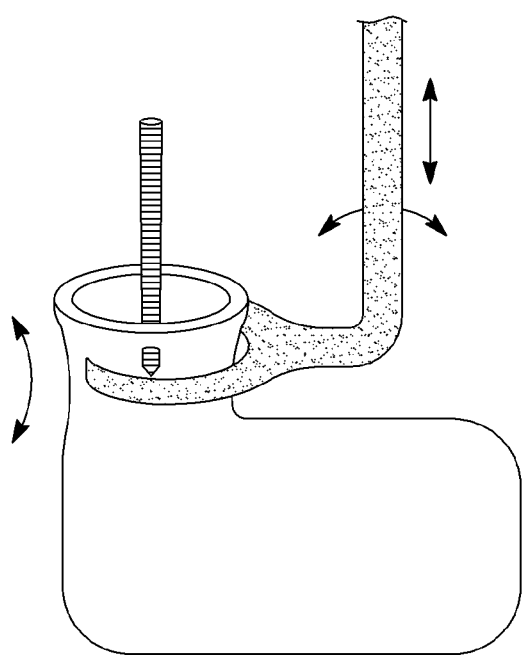
FIG. 22 is an oblique view of a portion of a vertebra, a pedicle instrument or screw, and the recording electrode.

FIG. 22 is an oblique view of a portion of a vertebra, a pedicle instrument or screw, and the recording electrode. The pedicle instrument can be seen penetrating the wall of the pedicle. The recording electrode can be moved up and down or around the pedicle to aid detection of the electrical impulse.

Figure 23:
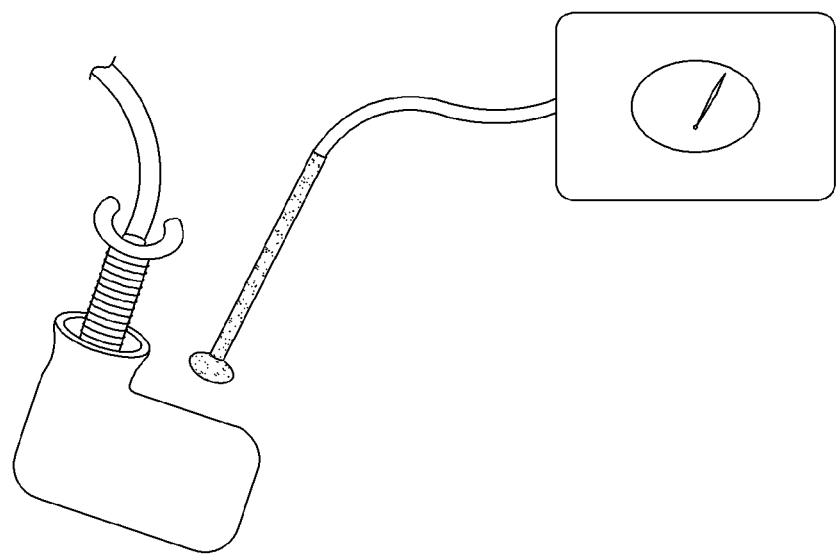
FIG. 23 is an oblique view of a portion of a vertebra, a pedicle screw, recording and stimulating electrodes use in an alternative embodiment of the apparatus.

FIG. 23 is an oblique view of a portion of a vertebra, a pedicle screw, recording and stimulating electrodes use in an alternative embodiment of the apparatus. The recording electrode detects impulses in the spinal canal, nerves, muscles, vertebrae, and other spinal tissues or tissues that surround the spine. For example, the recording electrode could be placed on a spinal nerve, or the thecal sac. Penetration of the pedicle screw or instrument would be predicted by recording electrical impulses from the spinal nerve or thecal sac after stimulating the pedicle instrument with electrical impulses with relatively low amplitudes. The recording electrode could also be placed in other spinal tissues such as the paraspinal muscles. Fluid or other material could be placed around the pedicle to aid the conduction of electrical impulses. For example, saline could be placed into the spinal canal during the stimulation and recording of the electrical impulses.

The invention also anticipates reversing the stimulating and the recording electrodes. That is, electrical impulses could be recorded from pedicle screws or instruments after stimulating a portion of the spine. For example, the outer wall of the pedicle could be stimulated. Additionally, the sensitivity and specificity of the apparatus, as well as prior art apparatus, could be improved by measuring the time between stimulation and recording the electrical impulses. Relatively high rates of electrical conduction suggest the pedicle screw or instrument lies on or too near a nerve.

Figure 24:
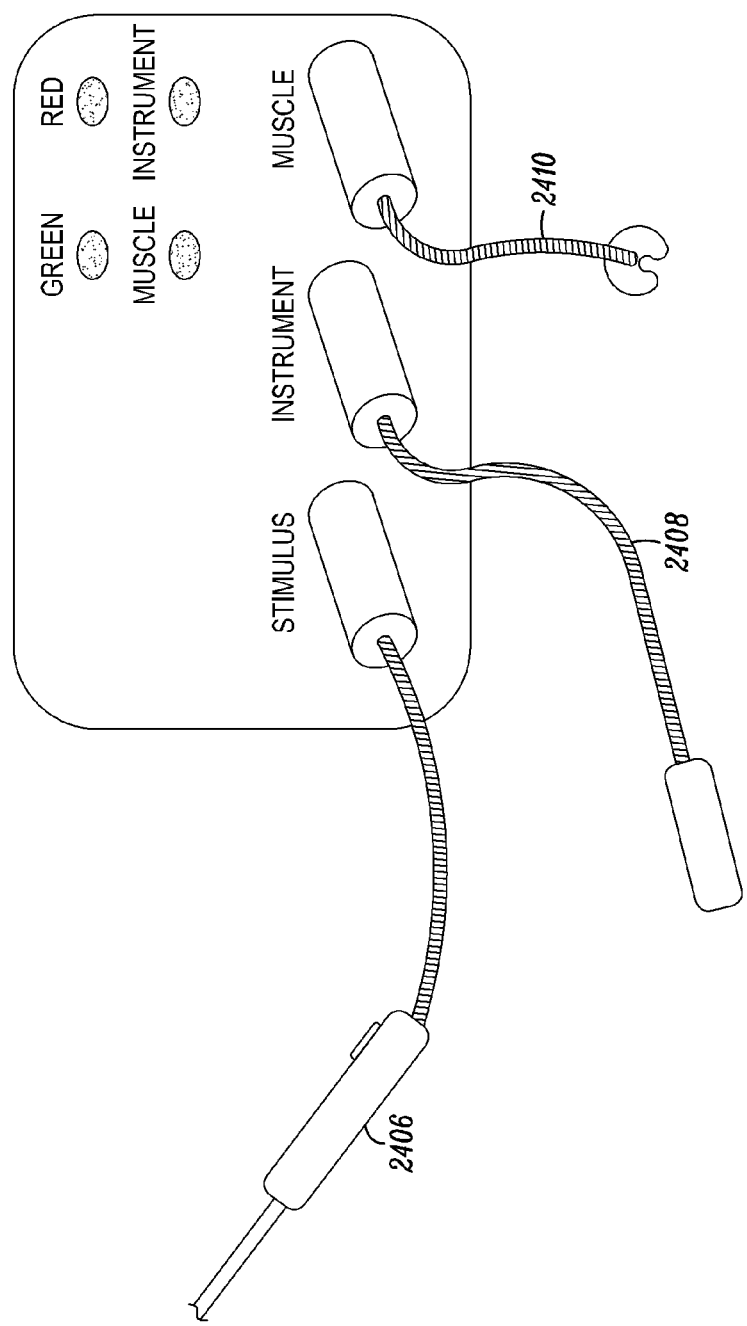
FIG. 24 is a view of apparatus according to the invention including a stimulating probe.

FIG. 24 is a view of apparatus according to the invention including a stimulating probe 2406 used to stimulate the spinal nerves (or other nerves). The stimulating probe is inserted into a port on the device marked "Stimulus". A recording cable 2408 is inserted into a port on the device marked "Instrument". The recording cable attaches to an instrument placed in the pedicle. For example, the "instrument" recording cable could be attached to the ratcheting instrument described in FIG. 16A. The ratcheting instrument is used to insert screws or taps into the vertebrae.

A second recording cable 2410 is inserted into a port on the device marked "Muscle". The "Muscle" recording cable may include a bundle of wires. The wires within the "Muscle" recording cable attach to leads placed over muscles. For example, the "muscle" leads could be placed over the myotomes of both lower extremities or both upper extremities. Alternatively, the "Muscle" cable could be attached to leads over the gluteal muscles, the paraspinal muscles, or tissues of the body.

A green indicator light indicates safe placement of the pedicle instrument. The green light illuminates if the "Muscle" recording cable sends an electrical impulse into the device after stimulation of a spinal nerve (alternatively other nerves could be stimulated) and the "Instrument" recording cable does not send an electrical impulse into the device after stimulation of the spinal nerve. A 6 mA stimulus could be delivered to the stimulus probe. Alternative stimuli between 0.01 mA to 40 mA could be delivered.

A red indicator light indicates a potentially misplaced pedicle instrument. The red light illuminates if the "Instrument" recording cable sends an electrical impulse into the device after stimulation of the spinal nerve or the "Muscle" recording cable fails to send an electrical impulse into the device. Two additional lights are used to determine why the red light illuminated. A "Muscle" light illuminates if the "Muscle" recording cable fails to send an electrical impulse into the device. Failure of the "muscle" recording cable to send an electrical impulse into the device suggests the nerve was not properly stimulated. An "Instrument" light illuminates if the "Instrument" cable sends an electrical impulse into the device. Illumination of the "Instrument" light alerts the surgeon the pedicle instrument has received an electrical impulse. The pedicle instrument receives an electrical impulse, if the instrument has breached the walls of the pedicle and the instrument is lying against the stimulated nerve. The device may also have ports that receive ground and reference electrodes.

Existing systems monitor all of the myotomes of both extremities. An electrical stimulus is delivered to the instrument within the pedicle. Detection of the electrical impulse after low levels of stimulation, for example 8 mA, in any myotome is indication of a potentially misplaced pedicle instrument. A preferred embodiment of this invention records from the instrument or screw within the pedicle rather than stimulating the instrument or screw within the pedicle. Recording leads over the muscles are used to confirm an electrical impulse has been applied to a spinal nerve (or other nerve). As such, recording a stimulus from any muscle in the extremities or potentially other muscles such as the gluteal or paraspinal muscles indicates the stimulus has been properly delivered. Recording from fewer, multiply innervated muscles, simplifies the device. Recording from fewer muscles and recording from the gluteal or paraspinal muscles also assists the surgeon. The present invention decreases the amount of time surgeons must spend applying the recording leads over multiple myotomes of both extremities while using prior art systems. The simplicity of the device enables surgeons to test and monitor their patients. The device does not require a highly compensated Neurophysiologist to interpret the data. Other embodiments of the invention eliminate the need to monitor any of the muscles.

Figure 25:
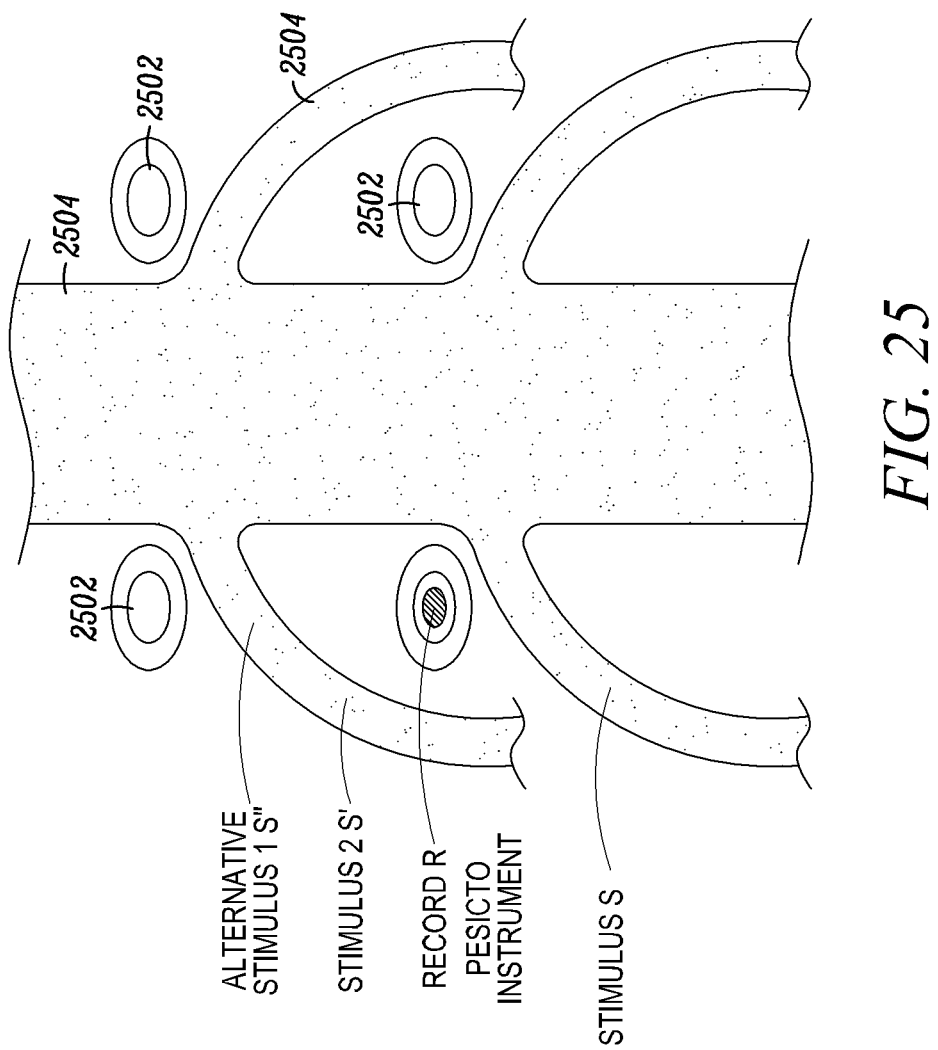
FIG. 25 is a view of the posterior aspect of the spine.

FIG. 25 is a view of the posterior aspect of the spine. The lamina have been removed to better illustrate the pedicles 2502 and the nerves 2504. The black circle in the center of one of the white circles indicates the cross section of an instrument within the pedicle (for example) a screw, tap, or curette.

In the embodiment of the invention depicted in FIG. 24, an electrical stimulus is delivered to the lower spinal nerve at point S. A recording electrode is attached at R to the instrument within pedicle. One or more additional recording electrodes are placed over muscles. A second stimulus is delivered to the spinal nerve at S', or, alternatively at S". If the pedicle instrument breaches the medial wall (spinal canal side) or the inferior wall of the pedicle, and the instrument lies against the spinal nerve, stimulation of the lower spinal nerve will stimulate the instrument in the pedicle. If the pedicle instrument breaches the lateral or superior wall of the pedicle, and the instrument lies against the spinal nerve, stimulation of the upper spinal nerve will stimulate the instrument within the pedicle. Instruments in adjacent pedicles on the same side of the spine may be tested simultaneously by stimulating a single spinal nerve. For example, stimulation of the L4 nerve simultaneously tests the integrity of the medial and inferior walls of the L4 pedicle and the superior and lateral walls of the L5 pedicle. Simultaneous testing of instruments within the pedicles requires a multi-channel device.

Prior art systems may detect a hole or a crack in a pedicle, but they do not indicate the location of the crack or hole in the pedicle. If surgeons know the location of the hole in the pedicle, then they can reposition a screw and safely direct the screw away from the hole in the pedicle. This invention helps surgeons determine if the misplaced pedicle instrument was placed through the inferior and/or the medial surface of the pedicle or through the superior and/or lateral wall of the pedicle.

Figure 26:
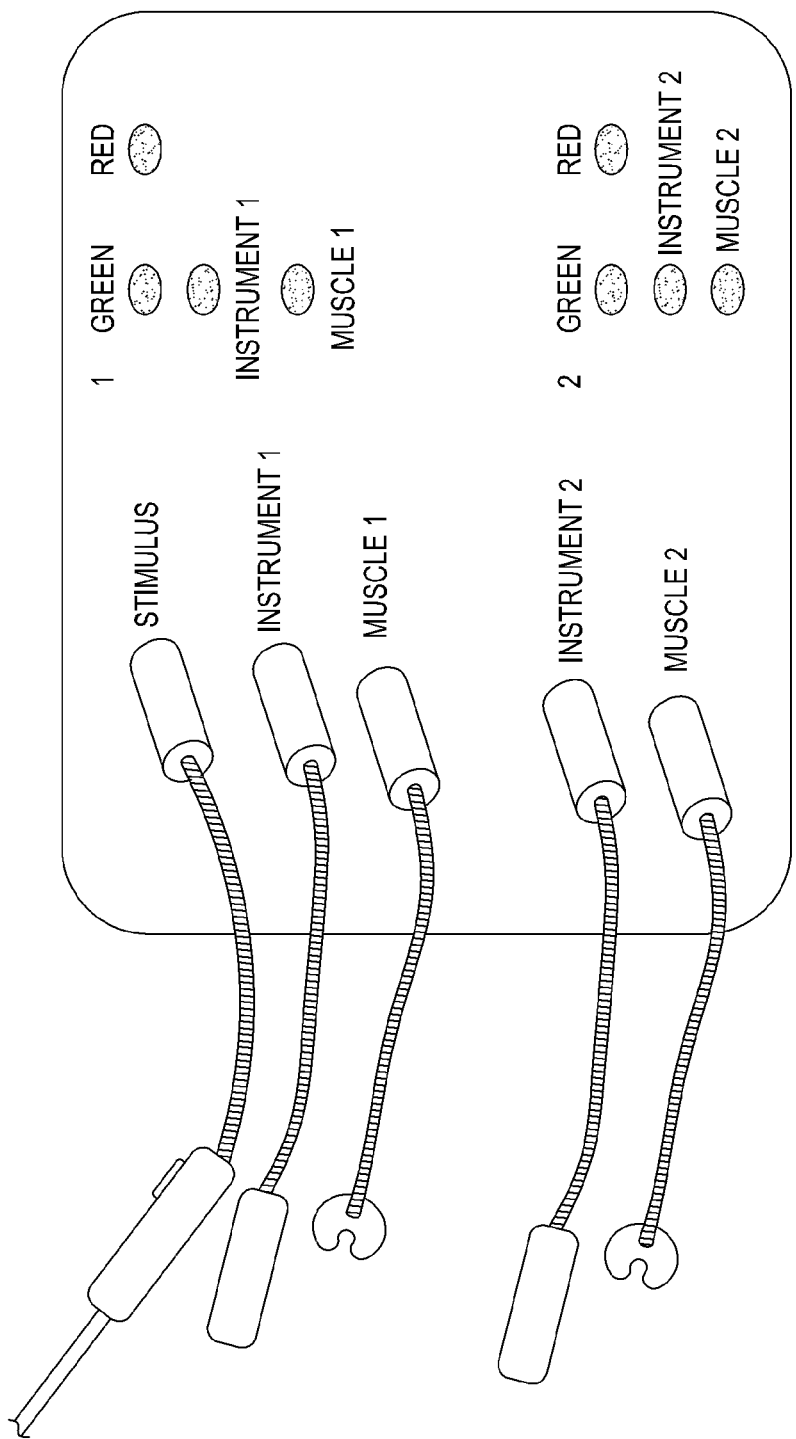
FIG. 26 is the view of the front of an alternative embodiment of the device drawn in FIG. 24.

FIG. 26 is the view of the front of an alternative embodiment of the device drawn in FIG. 24. The multi-channel device can be used to simultaneously test instruments in more than one pedicle. The cables extending from ports on right side of the device marked "Instrument 1" and "Instrument 2" can be attached to instruments in different pedicles. The stimulus probe can be used to deliver electrical impulses to a spinal nerve. The cables extending from the ports marked "Muscle 1 & Muscle 2" can be attached to surface electrodes over muscles supplied by the stimulated nerve. A single recording electrode may also be used when testing the instruments in two pedicle screws. For example, the cable attached to "Instrument1" could be attached to a tap in the left L4 pedicle.

The cable attached to "Instrument 2" could be attached to a screwdriver attached to a pedicle screw in the left L5 pedicle. The cables extending from the "Muscle 1" and/or "Muscle 2" ports could be attached to needle electrodes placed into the Gluteus Medius and the Gluteus Maximus Muscles of the left buttock. The Gluteus Medius is innervated by the superior gluteal nerve. The superior gluteal nerve arises from the L4, L5, & S1 nerves. The Gluteus Maximus is innervated by the inferior gluteal nerve. The inferior gluteal nerve arises from the L5, S1, and S2 nerves. Surface electrodes could be used rather than needle electrodes. A stimulus could be applied to the left L4 nerve root. The L4 nerve root courses along the inferior and medial surfaces of the L4 pedicle, and the superior and lateral portion of the L5 pedicle.

The indicator lights are similar to the indicator lights drawn in FIG. 24. If both green lights illuminate, then device did not detect electrical impulses from either instrument in the pedicles, and the device detected an electrical impulse from the recorded muscles. The device may use a reference recording lead to compare to the muscle recording lead. The device may contain a microprocessor. If the muscle recording lead receives a much stronger impulse than the reference electrode receives, then the nerve has likely been stimulated properly. Alternatively, the microprocessor may compare the impulses received by the recording electrodes to reference values. The reference values enable the device to indicate if the nerve has been properly stimulated or the soft tissues around the nerve were mistakenly stimulated. The device may use a ground lead.

The red light by the large number one will illuminate if the instrument attached to the cable from the "Instrument 1" port receives an electrical impulse or the device fails to receive an impulse from both or either "Muscle" recording electrodes. Similarly, the red light by the large number two will illuminate if the instrument attached to the cable from the "Instrument 2" port receives an electrical impulse or the device fails to receive an impulse from both or either "Muscle" recording electrodes. The "Instrument 1 & 2" and the "Muscle 1 & 2" lights are used as described in the text of FIG. 24, to indicate if the instruments have been stimulated or the muscles were not stimulated.

Figure 27A:
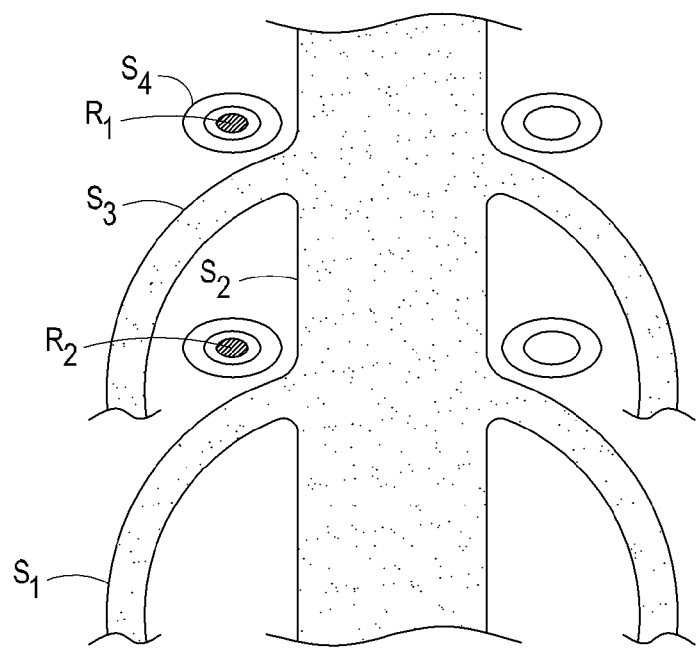
FIG. 27A is a posterior view of the spine similar to the view described in FIG. 25.

FIG. 27A is a posterior view of the spine similar to the view described in FIG. 25. The dark circles represent instruments in the pedicles. R1 and R2 represent recording electrodes that are attached to the instruments in the pedicles. S1, S2, & S3 represent a few of the possible stimulation sites. The figure illustrates a nerve may be stimulated below the pedicle, at the level of the pedicle, or above the pedicle. Stimulation of the nerve below the pedicle relies on transmission of the impulse in a caudal direction to test the superior and lateral aspects of the pedicle below the stimulated nerve and transmission of the impulse in a caudal direction to stimulate the muscle. Stimulation of the nerve below the pedicle relies on transmission of the impulse in a cephalic direction to test the inferior and medial surfaces of the pedicle above the stimulated nerve. Spinal nerves carry electrical impulses in both cephalic and caudal directions. Motor portions of the nerves transmit impulses away from the spinal cord to the muscles (caudal direction). Sensory portions of the nerves transmit impulses from the sensation receptors to the spinal cord (cephalic direction). The device drawn in FIG. 26 could be used to test the instruments in the adjacent pedicles drawn in FIG. 27A. A single stimulus delivered at S3 would test the instruments in both pedicles. Additional stimulus sites could be used to complete the testing. For example, stimulus sites S4 and S2 could be used to complete the testing.

Figure 27B:
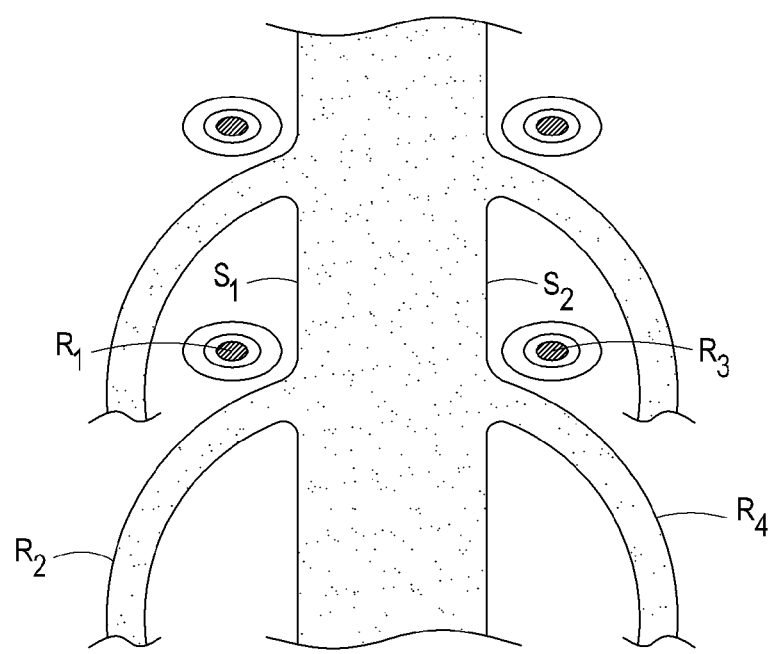
FIG. 27B is a posterior view of the spine as described in FIG. 27A.

FIG. 27B is a posterior view of the spine as described in FIG. 27A. The cross sections of pedicle instruments are seen in all of the pedicles. The drawing illustrates other embodiments of the invention. The embodiments drawn in FIG. 27B do not require monitoring the muscles in the extremities. In one embodiment of the invention the recording electrodes are placed in or over the nerves. Techniques well know to those specialists who perform EMG testing could be used to locate the nerves. Alternatively, the electrodes could be placed on or in the nerves under direct observation.

A stimulus is applied at S1. The recording electrodes are attached to the instrument in the pedicle (R1) and another portion of the stimulated nerve. If the R2 electrode detects the stimulated impulse and the R1 electrode does not detect the impulse, then it is unlikely the pedicle instrument is contacting the stimulated nerve. A multi-channel device could be used to test the instruments in more than one pedicle simultaneously. The R2 electrode could be placed in a spinal nerve or a peripheral nerve that has components that arise from the stimulated nerve. For example, for testing the pedicles in the lumbar spine, the R2 electrode could be placed in the sciatic nerve (L4, L5, S1, S2, & S3) or branches from the sciatic nerve, the femoral nerve (L2, L3, & L4) or branches from the femoral nerve, or other nerves. The spinal nerve components that form the sciatic and femoral nerves are listed in parentheses behind the words sciatic nerve and femoral nerve respectively. Naturally other nerves would be stimulated and recorded when testing instruments in the cervical and thoracic spine.

The invention is more sensitive and more accurate than prior-art devices. Prior-art devices may record a false positive if electrical impulses are delivered through a crack in the pedicle, but the instrument is contained within the pedicle. The present invention allows testing with smaller electrical impulses. The smaller impulses are less likely to stimulate a pedicle instrument through cracks in the pedicle. Prior art devices may record a false negative if the recording electrodes over the muscles in the extremities fail to detect an impulse. As noted previously, nerves that conduct impulses poorly, poor conduction through the surface electrodes, etc., may falsely indicate the instrument is safely contained in the pedicle.

Prior-art systems generally send multiple stimuli of increasing amplitude into the instrument within the pedicle. Prior art systems attempt to record the amount of stimuli necessary to record the impulse over the lower extremities. Recording an impulse over the lower extremities decreases the probability of a false negative result. Stimulating pedicle instruments with multiple stimuli with increasing amplitude is time consuming and requires sophisticated software. The present invention improves upon prior art devices by generally only requiring the application of a single stimulus per pedicle instrument undergoing testing. Some embodiments of the invention allow testing pedicle instruments in multiple vertebrae with the application of a single stimulus.

Note that the invention may also be used to test nerves while retracting nerves or performing other spinal procedures. The distance between S1 and R2 could be predetermined. In fact, S1 and R2 could extend from the same instrument. Electrical impulses could be periodically delivered to the nerve at S1 during surgery. For example, the electrical impulses could be delivered at a frequency of one per minute. The microprocessor within the monitor could signal an alarm, for example, illuminate a light bulb, if the amplitude of the impulse detected at R2 decreased when compared to a reference amplitude obtained by stimulating the nerve before manipulating the nerve during the operation. The microprocessor could also cause an alarm to signal if the time between the stimulus delivered at S1 and recorded at R2 increased when compared to a reference time obtained for the nerve before manipulating the nerve during the operation.

Standard reference amplitudes and velocities may also be preprogrammed into the microprocessor. Standard reference velocities require fixed distances between S1 and R2. The S1 impulse could be delivered through a nerve root retractor or a stimulus probe. A stimulus delivering retractor is drawn in FIG. 37. As noted above, R2 may lie anywhere along the course of the spinal nerve, nerves supplied by the spinal nerve, or muscles supplied by the spinal nerve. The device alerts surgeons of potential nerve injury before the nerve injury occurs. For example, excessive retraction of a nerve root may injure the nerve root. The device detects diminished nerve function within seconds or minutes of the excessive retraction. Embodiments of the invention for use with peripheral nerves are described in FIG. 36.

In the drawings, R4 represents an alternative recording position. One or more R4 electrodes could be placed over or in muscles of the body including muscles in the extremities, the muscles in the buttock, the muscles about the shoulder, or muscles about the spine. In contrast to prior-art devices, the R4 electrode may be used to confirm the nerve has been properly stimulated. Any muscle innervated by the stimulated muscle may be monitored. A single muscle that is supplied by multiple nerve roots may be monitored while testing instruments in pedicles at different levels of the spine. For example, the Gluteus Medius muscle could be monitored to confirm the L4, L5, or S1 nerves have been successfully stimulated. The gluteal muscles and the skin over the muscles are easily reached during surgeries on the lumbar spine. Prior-art systems require monitoring of many muscles of the body. Failure to detect stimulation of one of the muscles may lead to a false negative reading. A false negative reading fails to properly detect an instrument, such as a pedicle screw, is compressing or injuring a nerve. Prior-art systems typically require monitoring over four separate locations over each extremity. Preparing the skin over multiple sites and placing the electrodes over multiple sites is time consuming.

The present invention alerts surgeons if the R4 electrode is improperly placed or if the R4 electrode/electrodes has/have shifted during the operation. The red light on the device and the muscle light on the device illuminate if the R4 electrode does not record an impulse. The novel invention enables surgeons to monitor the paraspinal muscles. The paraspinal muscles area easily accessible in the surgical field. Prior art devices do not use the paraspinal muscles. Surgical exposure of the spine may injure the paraspinal muscles or the nerves to the muscles. Injury to the nerves to the paraspinal muscles or injury of the paraspinal muscles may cause prior art devices and methods to yield a false negative result, if the devices fail to record an impulse. Failure of prior art methods and devices to detect stimulation of the paraspinal muscles could indicate: (a) that the pedicle instrument is contained within the pedicle, (b) the nerve to the paraspinal muscle is not functioning properly, (c) the paraspinal muscles are not functioning properly or, (d) the stimulated muscle has not been recorded. Explanations (b), (c), and (d) lead to false negative results. Thus, prior-art systems do not monitor the paraspinal muscles. The present invention alerts the surgeon if injury to the nerves to the paraspinal muscles or the paraspinal muscles precludes monitoring the muscles, If the surgeon is unable to detect recordings from the paraspinal muscles after delivering a stimulus to the nerves, then the surgeon is alerted to monitor other muscles, such as the gluteal muscles. The ventrally, segmentally, innervated intertransversalis muscles are monitored in one embodiment of the invention. Other paraspinal muscles may be monitored.

Figure 28:
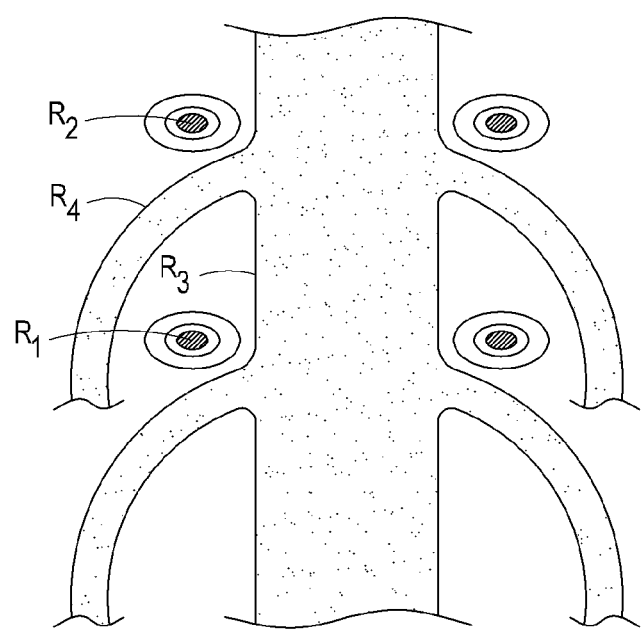
FIG. 28 is a posterior view of the spine, similar to the view drawn in FIG. 27B.

FIG. 28 is a posterior view of the spine, similar to the view drawn in FIG. 27B. An alternative embodiment of the invention is illustrated in the drawing. S1 represents stimulation of a peripheral nerve such as the sciatic nerve, femoral nerve, branches the sciatic nerve, branches of the femoral nerve, or other peripheral nerve. R3 & R4 represent recording sites on or in the spinal nerves. Alternative R3 & R4 sites include nerves within the thecal sac, the spinal cord, or the brain. The R3 & R4 sites are monitored to confirm the nerve has been stimulated correctly. The R1 & R2 are monitored to detect stimulation of the instruments within the pedicles. A single electrical stimulus from S1 could be used to test multiple pedicles simultaneously. Stimulation of the sciatic nerve may allow simultaneous testing of the pedicles near the L4, L5, S1, S2, & S3 nerves. Stimulation of the femoral nerve may allow testing of the pedicles near the L2, L3, and L4 nerves. A multi-channel device allows simultaneous testing of multiple pedicles.

Figure 29:
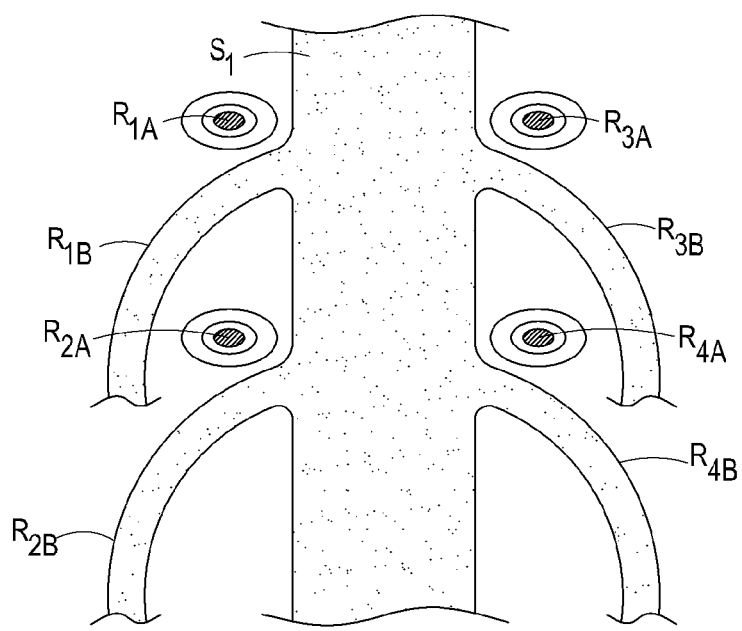
FIG. 29 is a posterior view of the spine similar to the view drawn in FIG. 28.

FIG. 29 is a posterior view of the spine similar to the view drawn in FIG. 28. The alternative embodiment of the invention stimulates multiple spinal nerves simultaneously. S1 represents a stimulus delivered over the nerves in the thecal sac, the spinal cord, or the brain. An electrical or magnetic stimulus may be used. R1B, R2B, R3B, & R4B are recording sites to confirm the spinal nerves near the pedicles undergoing testing are properly stimulated. R1A, R2A, R3A, & R4A are recording sites from the instruments that lie within the pedicles. If R1B, R2B, R3B, or R4B fail to detect an impulse, the device will alert the surgeon that the pedicle instruments at the R1A, R2A, R3A, or R4A sites respectively, has not been adequately tested. Failure to detect an impulse at a RnB site signals the stimulus was not applied to the surface of the pedicle by the nerve monitored by the RnB electrode. A S1 needle electrode may be placed through the dura. The S1 site may be cephalad or caudal to the tested pedicles. If all RB sites record impulses and none of the RA sites record impulses, then all of the instruments are likely contained within the pedicles. A multi-channel device, with at least four groups of alarm lights like those illustrated in FIG. 24, could be used in this embodiment of the invention.

Figure 30:
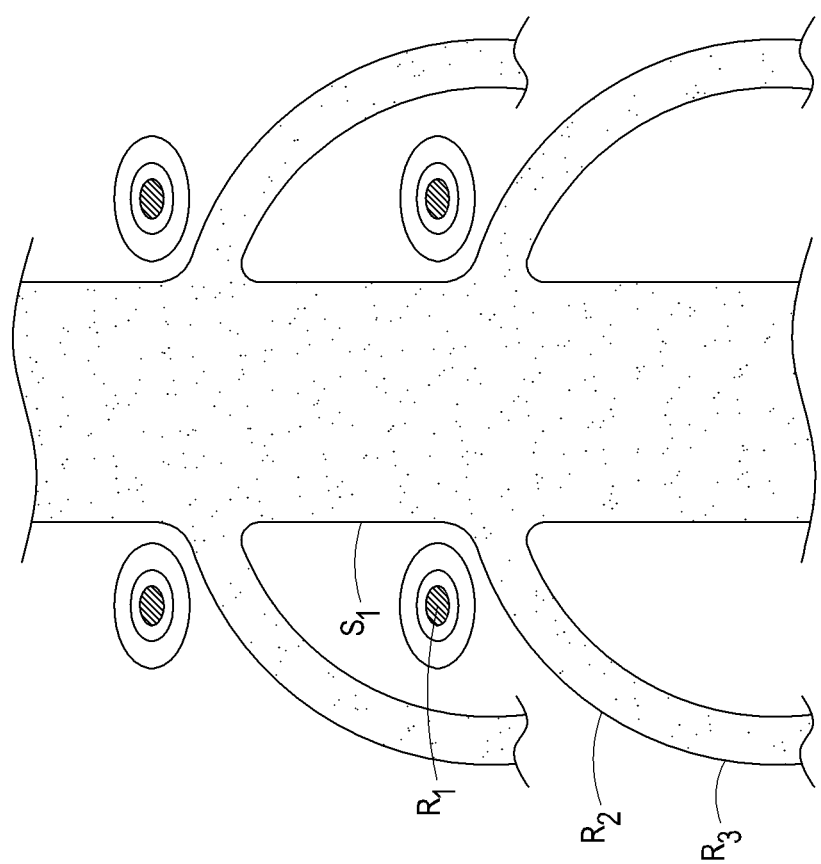
FIG. 30 is a posterior view of the spine, similar to the view drawn in FIG. 29, showing the alternative use of a reference electrode.

FIG. 30 is a posterior view of the spine, similar to the view drawn in FIG. 29, showing the alternative use of a reference electrode. A microprocessor within the device compares the impulse detected by the R2 electrode to the impulse detected by the reference (R3) electrode. The microprocessor triggers an alarm, such as illuminating a light bulb, if the stimulus received by R2 is below a preset value or the stimulus received by R2 is near or below that received by R3. The alarm alerts the surgeon that the electrodes at the R2 or S1 sites are not properly contacting the spinal nerve.

Figure 31:
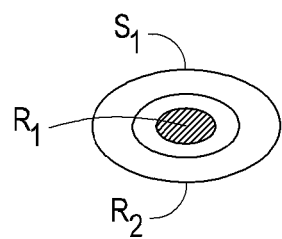
FIG. 31 is an axial view of a pedicle.

FIG. 31 is an axial view of a pedicle. The drawing illustrates an alternative embodiment of the invention. The black circle represents the cross section of an instrument in the pedicle. S1 represents a stimulation site. R1 represents a recording site on the instrument in the pedicle. R2 represent a recording site on the pedicle. If the R1 electrode detects a smaller signal than the R2 electrode the instrument is likely contained in the pedicle.

Figure 32A:
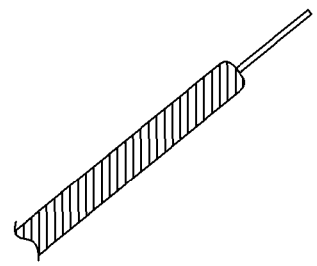
FIG. 32A is a lateral view of a needle-tipped stimulating or recording electrode.
Figure 32B:
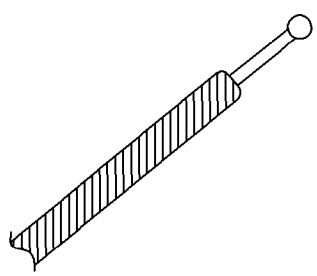
FIG. 32B is a lateral view of an alternative embodiment of the tip of the electrode drawn in FIG. 32A.
Figure 32C:
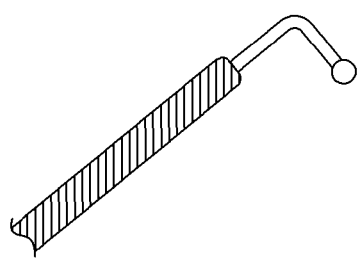
FIG. 32C is a lateral view of an alternative embodiment of the tip of the electrode drawn in FIG. 32A.

FIG. 32A is a lateral view of a needle-tipped stimulating or recording electrode. The area of the drawing with diagonal lines represents insulating material. The needle tipped electrode is generally placed in nerves or muscles. FIG. 32B is a lateral view of an alternative embodiment of the tip of the electrode drawn in FIG. 32A. The balled tipped probe is generally placed on nerves or muscles. FIG. 32C is a lateral view of an alternative embodiment of the tip of the electrode drawn in FIG. 32A. The curved tip is easier to insert through the neuroforamina. The tip may help the surgeon direct the electrode to the S1 position drawn in FIG. 30.

Figure 33:
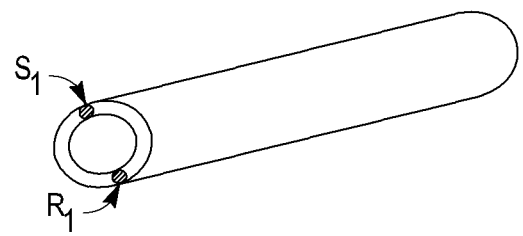
FIG. 33 is an oblique view of an alternative embodiment of the invention.

FIG. 33 is an oblique view of an alternative embodiment of the invention. This embodiment of the invention demonstrates the use of stimulating (S1) and recording (R1) electrodes in an instrument. For example the instrument may be a cannula as drawn in FIG. 33. Other than the electrodes, the instrument is made of a non-electrical conducting material in the preferred embodiment of the device. A monitor with microprocessor measures the amplitude and velocity of an impulse delivered from S1 to R1. Rapid transfer of a high amplitude impulse suggests the cannula is against a tissue that readily transfers impulses. Nerves transmit impulses better than muscles transmit impulses. The novel cannula could be used to alert surgeons when the instrument is against a nerve. Surgeons could use the novel cannula to navigate between the nerves in muscles. For example, surgeons could use the device for transpsoas approaches to the spine.

Figure 34A:
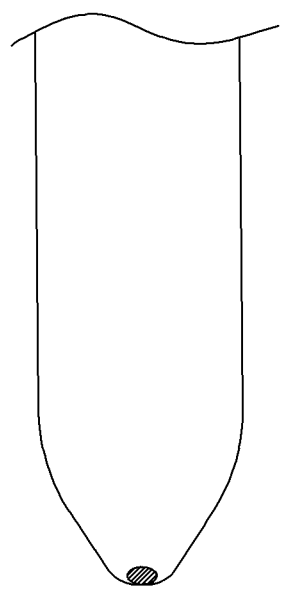
FIG. 34A is a lateral view of another embodiment of the invention drawn in FIG. 33.
Figure 34B:
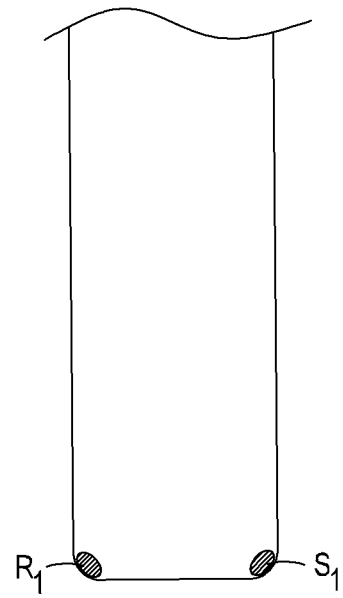
FIG. 34B is an anterior view of the embodiment of the device drawn in FIG. 34A.
Figure 34C:
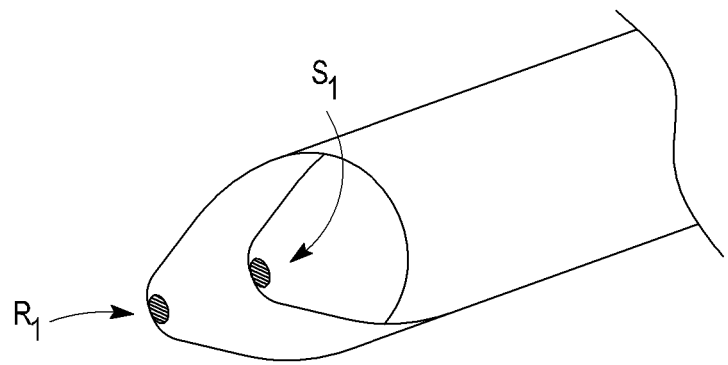
FIG. 34C is an oblique view of the embodiment of the device drawn in FIG. 34A.
Figure 35:
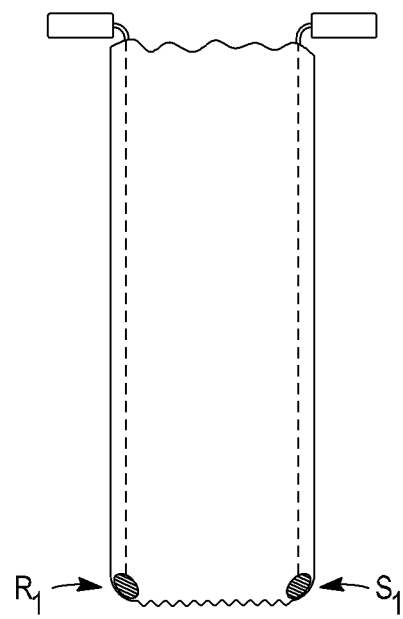
FIG. 35 is an anterior view of another embodiment of the device drawn in FIG. 33.

FIG. 34A is a lateral view of another embodiment of the invention drawn in FIG. 33. Recording and stimulating electrodes are used in the walls of a stylet or a blunt dissector. Other than the electrodes, the stylet or dissector is made of a material that conducts electricity poorly. The stylet can be used within a cannula. The blunt tip helps surgeons separate the fibers of muscles. The electrodes and the monitor alert surgeons when the instrument lies against a nerve. FIG. 34B is an anterior view of the embodiment of the device drawn in FIG. 34A. FIG. 34C is an oblique view of the embodiment of the device drawn in FIG. 34A. FIG. 35 is an anterior view of another embodiment of the device drawn in FIG. 33. The electrodes are incorporated into the ends of a retractor.

Figure 36:
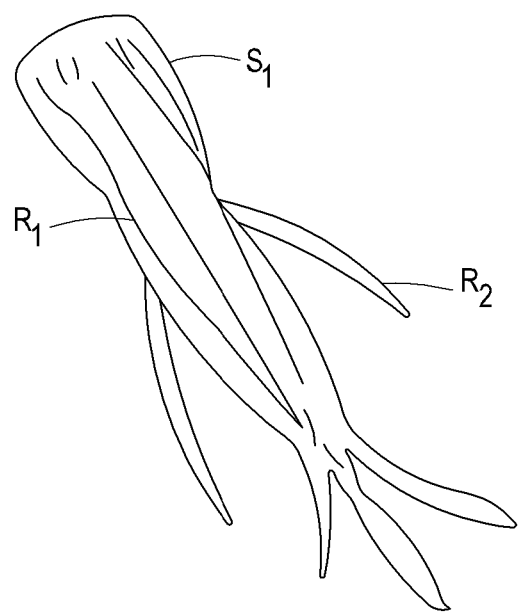
FIG. 36 is a posterior view of a peripheral nerve and another embodiment of the invention.

FIG. 36 is a posterior view of a peripheral nerve and another embodiment of the invention. This embodiment of the invention may be used to protect peripheral nerves during non-spinal operations. The nerve is stimulated at one location S1. Recording electrodes/electrode are placed in another location along the nerve or a branch of the nerve (R1). Alternatively recording electrodes/electrode may be placed in muscles that are supplied by the stimulated nerve (R2). A device, with a microprocessor, delivers electrical impulses at S1 periodically during the operation. For example, the device may deliver one impulse per minute. The device measures the amplitude of the impulses recorded at R1 and/or R2 and the time between the delivery of the stimulus and recording of the stimulus. The device triggers an alarm, for example illuminates a light bulb, if the amplitude or velocity of the transmitted stimulus deteriorates during the surgical procedure.

The microprocessor may also be programmed to compare the recorded values for the stimulus to standard values. The distance between S1 and R1 or R2 could be fixed or measured to enable the microprocessor to calculate velocity figures. For example, this embodiment of the device could be used during hip replacement surgery. A needle electrode (S1) could be placed into the sciatic nerve at the level of the sciatic notch. The S1 electrode could be sutured into place. Alternatively, the mechanisms use to hold pacemaker electrodes in position could be used to hold the S1 electrode in the tissues near the sciatic nerve while the tip of the S1 electrode lies in the nerve. The device would quickly alarm the surgeon if sciatic nerve function deteriorated during surgery. The device would alert the surgeon to diminish traction on the sciatic nerve before the injury became permanent. This embodiment may be used on other peripheral nerves in the body. It may also be used to detect additional causes of nerve injury such as pressure on the nerve or surgical dissection around the nerve.

Figure 37:
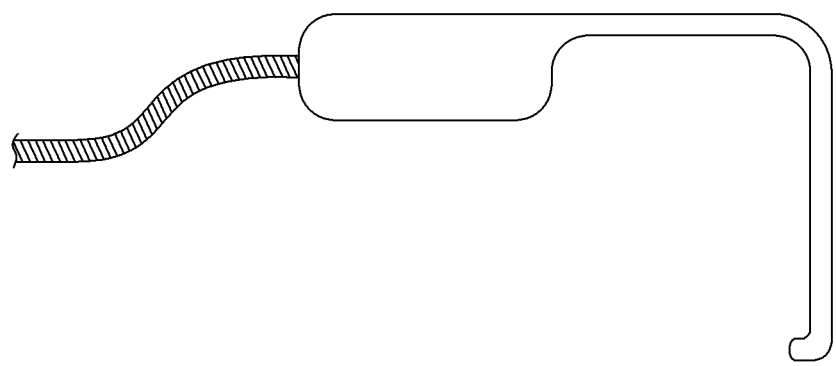
FIG. 37 is a lateral view of a nerve root retractor that stimulates the spinal nerves.

FIG. 37 is a lateral view of a nerve root retractor that stimulates the spinal nerves. The retractor can be used to deliver the stimulus at the S1 site as described in FIG. 30.

According to this invention, electric impulses may be recorded from an instrument placed into and possibly through the pedicle of a vertebra. Peripheral nerves, spinal nerves, the sciatic nerve, the femoral nerve, or a plexus of nerves may be stimulated. Recording electrodes are also placed over spinal nerves. A recording electrode may be placed through the dura. If the recording electrode over, or within, a nerve detects an impulse transmitted through the nerve and the recording electrode on an instrument placed into a pedicle does not detect an impulse, then it is likely the instrument within the pedicle does not breach the walls of the pedicle. Alternatively, the spinal nerves could be stimulated with recording electrodes placed over or in peripheral nerves, the nerves in the thecal sac, and the instrument/instruments in the pedicles.

Stimulation and/or recording electrodes can be used over the dura or through the dura cephald and/or caudal to the level the pedicle screw or screws are inserted. Multiple pedicle screws could be tested simultaneously by a single stimulating impulse. For example, a trans-dural stimulating electrode could be placed cephald to the pedicle screws. A second trans-dural recording electrode could be placed caudal to the pedicle screws. Alternatively, multiple recording electrodes could be placed over or in the spinal nerves near the pedicle screws. The recording electrodes listed above could be changed to stimulating electrodes and the stimulating electrodes listed above could be changed to recording electrodes. If recording electrodes placed on instruments within the pedicles do not detect an electrical impulse, but the recording electrodes over or within the nerves detect an impulse, then the screws, curettes, or taps are likely within the pedicles. Testing of the invention will likely determine thresholds (for stimulation and recording) at which penetration of the pedicle wall by an instrument is unlikely. Techniques well known to those who perform EMG testing could be used to help locate spinal and peripheral nerves.

An electrode placed over or within a myotome may be used to confirm stimulation of a nerve. For example, if an electrode over the L5 myotome detects an impulse applied to the L5 nerve and a recording electrode from an instrument in a pedicle near the L5 nerve does not record an impulse, it is unlikely the instrument within the pedicle near the L5 nerve penetrates the wall of the pedicle. The invention eliminates the need for repeated stimulation at successively higher impulses as used in prior art systems. Prior art systems use successively higher impulses to record a value in the extremities in an effort to avoid a false negative. Failure to record a stimulus over the myotome in prior art systems may confirm the instrument does not penetrate the walls of the pedicle. Alternatively, failure to record a stimulus over the myotome in prior art systems may indicate a problem with the conductivity of the nerve, the junction between skin and the electrode, or other technical problem.

Recording and/or stimulating electrodes can be placed in or over the tissues about the spine including the disc, the gluteal muscles, muscles about the hip or shoulder girdle, or the extremities.

Velocity calculations and measurements (of transmittance of the electrical impulse) may also be used. A single monitor or instrument may have recording and stimulating electrodes. A fixed distance between the recording and stimulating electrodes would ease velocity calculations. For example, a non-conducting cannula with one or more stimulating electrodes and one or more recording electrodes may be used in transpsoas approaches. An impulse that travels with high velocity from the stimulating electrode to the recording electrode suggests the cannula is near or against a nerve. Stimulation may be in the range of 0.01 mA-50 mA.

What is claimed is:

1. An instrument for determining directionality during surgery, comprising:
    a rigid probe member having a distal end having a circumference and a longitudinal axis, said distal end circumferentially insulated and configured for advancement into a pedicle and rotatable in the pedicle, and an electrode region situated about only a portion of said circumference and extending along a portion of said longitudinal axis, said electrode region configured to transmit an electric stimulation signal radially from said longitudinal axis to a pedicle;
    a recording electrode; and
    a neurophysiology monitoring system communicatively linked to said probe and said recording electrode, and configured to record a stimulus received by the recording electrode caused by the electric stimulation signal of the probe member.

2. The instrument of claim 1, wherein said neurophysiology monitoring system determines the location of a pedicle breach by determining a threshold stimulation level at which muscles innervated by a nerve proximate said pedicle respond to said stimulation signal.

3. The instrument of claim 2, wherein said instrument indicates the location of said pedicle breach by determining the position of said electrode region about said longitudinal axis of said probe member when said stimulation threshold is lowest.

4. The instrument of claim 1, wherein a non-insulated area forms said electrode region.

5. The instrument of claim 1, wherein said probe member is insulated to prevent shunting of said stimulation signal along the length of said probe member.

6. The instrument of claim 1, wherein said probe member is electrically linked to said neurophysiology monitoring system via a connector attached to said probe member.

7. The instrument of claim 6, wherein said connector is a clip around at least a portion of said probe member.

8. The instrument of claim 1, wherein probe member further comprises a proximate end, and wherein the proximate end of the probe member and the distal end of the probe member are co-linear.

9. The instrument of claim 1, wherein the probe member comprises a handle having a circumference, and wherein the handle has a larger circumference than the distal end circumference.

10. The instrument of claim 1, wherein the electrode region has an electrode region distal end and an electrode region proximate end, and wherein the electrode region distal end is located at the probe member distal end.

11. The instrument of claim 1, wherein said electrode region is configured to transmit an electric stimulation signal perpendicularly from said longitudinal axis.

12. The instrument of claim 1, wherein said portion of said longitudinal axis has a constant diameter along the longitudinal axis.

* * * * *